US010098904B2

(12) United States Patent
Coates et al.

(10) Patent No.: US 10,098,904 B2
(45) Date of Patent: Oct. 16, 2018

(54) ZIDOVUDINE COMBINATION THERAPIES FOR TREATING MICROBIAL INFECTIONS

(71) Applicant: HELPERBY THERAPEUTICS LIMITED, London (GB)

(72) Inventors: Anthony Coates, London (GB); Yanmin Hu, London (GB)

(73) Assignee: HELPERBY THERAPEUTICS LIMITED, London (GB)

( * ) Notice: Subject to any disclaimer, the term of this patent is extended or adjusted under 35 U.S.C. 154(b) by 0 days.

(21) Appl. No.: 15/111,275

(22) PCT Filed: Jan. 29, 2015

(86) PCT No.: PCT/GB2015/050209
§ 371 (c)(1),
(2) Date: Jul. 13, 2016

(87) PCT Pub. No.: WO2015/114340
PCT Pub. Date: Aug. 6, 2015

(65) Prior Publication Data
US 2016/0331773 A1    Nov. 17, 2016

(30) Foreign Application Priority Data

Jan. 30, 2014  (GB) .................................. 1401617.4

(51) Int. Cl.
| A61K 31/7072 | (2006.01) |
| A61K 38/12 | (2006.01) |
| A61K 31/435 | (2006.01) |
| A61K 31/4525 | (2006.01) |
| A61K 31/496 | (2006.01) |

(52) U.S. Cl.
CPC ........ *A61K 31/7072* (2013.01); *A61K 31/435* (2013.01); *A61K 31/4525* (2013.01); *A61K 31/496* (2013.01); *A61K 38/12* (2013.01)

(58) Field of Classification Search
CPC .. A61K 31/7072; A61K 31/496; A61K 38/12; C07K 7/62
See application file for complete search history.

(56) References Cited

U.S. PATENT DOCUMENTS 6,974,585 B2    12/2005    Askill

FOREIGN PATENT DOCUMENTS

| WO | 95100999 | 4/1995 |
| WO | 2000028074 | 5/2000 |
| WO | 2005014585 | 2/2005 |
| WO | 2006048747 | 5/2006 |
| WO | 2007054599 | 2/2007 |

OTHER PUBLICATIONS

Jarvis et al. ("Rifapentine," ADIS New Drug Profile, 1998, vol. 56, No. 4, p. 607-616).*
Tascini et al. ("Synergistic Activity of Colistin plus Rifampin against Colistin-Resistant KPC-Producing Klebsiella pneumoniae," Antimicrobial Agents and Chemotherapy, Aug. 2013, vol. 57, No. 8, p. 3990-3993 2013).*
Elwell et al. ("Antibacterial Activity and Mechanism of Action of 3'-Azido-3'-Deoxythymidine (BW A509U)," Antimicrobial Agents and Chemotherapy, Feb. 1987, vol. 31, No. 2, p. 274-280).*
Doléans-Jordheim et al. "Zidovudine (AZT) has a bactericidal effect on enterobacteria and induces genetic modifications in resistant strains," Eur J Clin Microbiol Infect Dis, 2011, vol. 30, p. 1249-1256).*
Groicher et al., "The *Staphylococcus aureus* IrgAB Operon Modulates Murein Hydrolase Activity and Penicillin Tolerance", Journal of Bacteriology, 182(7):1794-1801 (2000).
Hu et al., "Increased levels of sigJ mRNA in late stationary phase cultures of *Mycobacterium tuberculosis* detected by DNA array hybridisation", FEMS Microbiology Letters, 202:59-65 (2001).
Hu et al., "Detection of mRNA Transcripts and Active Transcription in Persistent Mycobacterium tuberculosis Induced by Exposure to Rifampin or Pyrazinamide", Journal of Bacteriology, 182(22):6358-6565 (2000).
Hughes et al., "Carbon Starvation of *Salmonella typhimurium* Does Not Cause a General Increase of Mutation Rates", Journal of Bacteriology, 179(21):6688-6691 (1997).
Lee et al., "Synergistic Activity of Colistin and Rifampin Combination against Multidrug-Resistant *Acinetobacter baumannii* in an In Vitro pharmacokinetic/Pharmacodynamic Model", Antimicrobial Agents and Chemotherapy, 57(8):3738-3745 (2013).
Martinez et al., "Mutation Frequencies and Antibiotic Resistance", Antimicrobial Agents and Chemotherapy, 44(7):1771-1777 (2000).
Rifadin for Infusion 600mg, EMC, http://www.medicines.org.uk/emc/medicine/6435/SPC/Rifadin+For+Infusion+600mg/ (Feb. 11, 2017).
Spoering et al., "Biofilms and Planktonic Cells of Pseudomonas aeruginosa Have Similar Resistance to Killing by Antimicrobials", Journal of Bacteriology, 183(23):6746-6751 (2001).
Spratt, "Resistance to Antibiotics Mediated by Target Alterations", Science, 264:388-393 (1994).
Taddei et al., "cAMP-dependent SOS induction and mutagenesis in resting bacterial populations", Proc. Natl. Acad. Sci. USA, 92:11736-11740 (1995).
Tagliaferri et al., "Synergistic Activity of Colistin (COL) plus Rifampin (RIF) Against COL-Resistant (R) and Susceptible (S) KPC-producing *Klebsiella pneumoniae* (KPC-KP) clinical isolates", Abstract XP055154648, Abstract of the Interscience Conference on Antimicrobial agents and chemotherapy, 52:E796 (2012).
Tsiodras et al., "Linezolid resistance in a clinical isolate of *Staphylococcus aureus*", Research Letters, 358(9277):207-208 (2001).
Van Asselt et al., "Detection of penicillin tolerance in *Streptococcus pyogenes*", J. Med. Microbial., 38:197-202 (1993).
Pantopoulou et al., "Colistin offers prolonged survival in experimental infection by multidrug-resistant *Acinetobacter baumannii*: the significance of co-administration of rifampicin", International Journal of Antimicrobial Agents, 29:51-55 (2007).

(Continued)

*Primary Examiner* — Christina Bradley
(74) *Attorney, Agent, or Firm* — Sughrue Mion, PLLC

(57) ABSTRACT

The present invention relates to the use of a combination of an anti-retroviral agent such as zidovudine and anti-microbial agents for killing clinically latent microorganisms associated with microbial infections and to novel combinations comprising an anti-retroviral agent such as zidovudine and anti-microbial agents for the treatment of microbial infections.

16 Claims, 16 Drawing Sheets

(56) References Cited

OTHER PUBLICATIONS

Mascellino et al., "In vitro activity of zidovudine alone and in combination with ciprofloxacin against *Salmonella* and *Escherichia coli*", FEMS Immunology and Medical Microbiology, 7:23-28 (1993).

Keith et al., "In Vivo Efficacy of Zidovudine (3'-Azido-S'-Deoxythymidine) in Experimental Gram-Negative-Bacterial Infections", Antimicrobial Agents and Chemotherapy, 33(4):479-483 (1989).

Zhou et al., "Synergistic Antibiotic Combination Powders of Colistin and Rifampicin Provide High Aerosolization Efficiency and Moisture Protection", The AAPS Joumal, 16(1):37-47 (2014).

Motaouakkil et al, "Colistin and rifampicin in the treatment of nosocomial infections from multi-resistant *Acinetobacter baumannii*", Journal of Infection, 53:274-278 (2006).

Bassetti et al, "Colistin and rifampicin in the treatment of multidrug-resistant *Acinetobacter baumannii* infections", Journal of Antimicrobial Chemotherapy, 61:417-420 (2008).

Bhardwaj et al., "Piperine, a Major Constituent of Black Pepper, Inhibits Human P-glycoprotein and CYP3A4", The J. of Pharmacology and Experimental Therapeutics, 302(2):645-650 (2002).

Chitnis et al., "In Vitro Synergistic Activity of Colistin with Aminoglycosides, Beta-Lactams and Rifampin against multidrug-resistant Gram-negative Bacteria", J. of Chemotherapy, 19(2):226-229 (2007).

Davey et al., "Tolerance of *Pseudomonas aeruginosa* to killing by ciprofloxacin, gentamicin and imipenem in vitro and in vivo", J. of Antimicrobial Chemotherapy, 20:395-404 (1988).

Durante-Mangoni et al., "Colistin and Rifampicin Compared With Colistin Alone for the Treatment of Serious Infections Due to Extensively Drug-Resistant *Acinetobacter baumannii*: A Multicenter, Randomized Clinical Trial", Colistin and Rifampicin Against Acinetobacter, 57:349-358 (2013).

Coates et al., "The future challenges facing the development of new antimicrobial drugs", Nature Reviews, Drug Discovery, 1:895-910 (2002).

Fux et al., "Survival strategies of infectious biofilms", Trends in Microbiology, 13(1):34-40 (2005).

Gonzales et al., "Infections due to vancomycin-resistant *Enterococcus faecium* resistant to linezolid", Lancet, 357(9263):1179 (2001).

* cited by examiner

| Triple drug combination | Rifampicin | | | | | | | | | | | | HT0120663 |
|---|---|---|---|---|---|---|---|---|---|---|---|---|---|
| µg/ml | 1024 | 512 | 256 | 128 | 64 | 32 | 16 | 8 | 4 | 2 | 1 | 0 | 2 |
| Colistin 32 | 0.35 | 0.18 | 0.14 | 0.13 | 0.11 | 0.09 | 0.07 | 0.06 | 0.05 | 0.05 | 0.05 | 0.04 | |
| 16 | 0.23 | 0.16 | 0.13 | 0.13 | 0.12 | 0.09 | 0.07 | 0.06 | 0.05 | 0.04 | 0.04 | 0.04 | |
| 8 | 0.19 | 0.15 | 0.14 | 0.13 | 0.12 | 0.09 | 0.07 | 0.05 | 0.05 | 0.04 | 0.04 | 0.04 | |
| 4 | 0.17 | 0.14 | 0.13 | 0.13 | 0.11 | 0.08 | 0.07 | 0.05 | 0.05 | 0.04 | 0.04 | 0.04 | |
| 2 | 0.17 | 0.14 | 0.13 | 0.13 | 0.11 | 0.09 | 0.07 | 0.05 | 0.05 | 0.04 | 0.04 | 0.04 | |
| 1 | 0.17 | 0.15 | 0.13 | 0.13 | 0.11 | 0.09 | 0.07 | 0.05 | 0.05 | 0.24 | 0.24 | 0.24 | |
| 0.5 | 0.17 | 0.15 | 0.15 | 0.13 | 0.15 | 0.12 | 0.10 | 0.23 | 0.26 | 0.26 | 0.24 | 0.24 | |
| 0 | 0.18 | 0.16 | 0.28 | 0.18 | 0.60 | 0.13 | 0.18 | 0.66 | 0.47 | 0.30 | 0.19 | 0.11 | |

Figure 18

| Triple drug combination | Rifampicin | | | | | | | | | | | | HT0120663 |
|---|---|---|---|---|---|---|---|---|---|---|---|---|---|
| µg/ml | 1024 | 512 | 256 | 128 | 64 | 32 | 16 | 8 | 4 | 2 | 1 | 0 | 4 |
| Colistin 32 | 0.36 | 0.19 | 0.15 | 0.14 | 0.12 | 0.09 | 0.07 | 0.06 | 0.05 | 0.05 | 0.05 | 0.05 | |
| 16 | 0.23 | 0.16 | 0.14 | 0.14 | 0.12 | 0.09 | 0.07 | 0.05 | 0.05 | 0.05 | 0.04 | 0.05 | |
| 8 | 0.19 | 0.15 | 0.14 | 0.14 | 0.12 | 0.09 | 0.07 | 0.05 | 0.05 | 0.05 | 0.04 | 0.05 | |
| 4 | 0.18 | 0.15 | 0.14 | 0.13 | 0.11 | 0.09 | 0.07 | 0.05 | 0.05 | 0.04 | 0.04 | 0.05 | |
| 2 | 0.18 | 0.15 | 0.14 | 0.13 | 0.12 | 0.09 | 0.07 | 0.05 | 0.05 | 0.04 | 0.04 | 0.05 | |
| 1 | 0.18 | 0.15 | 0.13 | 0.13 | 0.12 | 0.09 | 0.07 | 0.05 | 0.05 | 0.05 | 0.07 | 0.45 | |
| 0.5 | 0.18 | 0.15 | 0.15 | 0.14 | 0.15 | 0.30 | 0.11 | 0.33 | 0.26 | 0.36 | 0.38 | 0.52 | |
| 0 | 0.19 | 0.16 | 0.23 | 0.86 | 0.45 | 0.51 | 0.43 | 0.18 | 0.14 | 0.36 | 0.38 | 0.36 | |

Figure 19

| Triple drug combination | Rifampicin | | | | | | | | | | | | HT0120663 |
|---|---|---|---|---|---|---|---|---|---|---|---|---|---|
| µg/ml | 1024 | 512 | 256 | 128 | 64 | 32 | 16 | 8 | 4 | 2 | 1 | 0 | 8 |
| Colistin 32 | 0.17 | 0.15 | 0.14 | 0.14 | 0.12 | 0.09 | 0.07 | 0.06 | 0.05 | 0.05 | 0.05 | 0.05 | |
| 16 | 0.17 | 0.15 | 0.14 | 0.14 | 0.12 | 0.09 | 0.07 | 0.05 | 0.05 | 0.04 | 0.04 | 0.04 | |
| 8 | 0.19 | 0.15 | 0.13 | 0.13 | 0.12 | 0.09 | 0.07 | 0.05 | 0.05 | 0.04 | 0.04 | 0.04 | |
| Colistin 4 | 0.17 | 0.15 | 0.14 | 0.14 | 0.12 | 0.09 | 0.07 | 0.05 | 0.05 | 0.05 | 0.04 | 0.04 | |
| 2 | 0.17 | 0.15 | 0.14 | 0.13 | 0.11 | 0.09 | 0.07 | 0.05 | 0.05 | 0.05 | 0.05 | 0.05 | |
| 1 | 0.17 | 0.15 | 0.14 | 0.13 | 0.12 | 0.09 | 0.07 | 0.05 | 0.05 | 0.05 | 0.05 | 0.05 | |
| 0.5 | 0.17 | 0.15 | 0.14 | 0.13 | 0.12 | 0.09 | 0.07 | 0.06 | 0.06 | 0.06 | 0.07 | 0.06 | |
| 0 | 0.18 | 0.15 | 0.15 | 0.13 | 0.12 | 0.09 | 0.09 | 0.07 | 0.06 | 0.07 | 0.07 | 0.07 | |

Figure 20

| Triple drug combination | Rifampicin | | | | | | | | | | | | HT0120663 |
|---|---|---|---|---|---|---|---|---|---|---|---|---|---|
| µg/ml | 1024 | 512 | 256 | 128 | 64 | 32 | 16 | 8 | 4 | 2 | 1 | 0 | 16 |
| Colistin 32 | 0.34 | 0.19 | 0.14 | 0.14 | 0.11 | 0.08 | 0.07 | 0.05 | 0.05 | 0.05 | 0.05 | 0.05 | |
| 16 | 0.23 | 0.16 | 0.14 | 0.13 | 0.12 | 0.09 | 0.07 | 0.05 | 0.05 | 0.05 | 0.04 | 0.05 | |
| 8 | 0.20 | 0.15 | 0.14 | 0.14 | 0.12 | 0.08 | 0.07 | 0.05 | 0.05 | 0.05 | 0.04 | 0.04 | |
| Colistin 4 | 0.18 | 0.15 | 0.14 | 0.14 | 0.12 | 0.08 | 0.07 | 0.05 | 0.05 | 0.05 | 0.04 | 0.04 | |
| 2 | 0.18 | 0.15 | 0.14 | 0.13 | 0.12 | 0.08 | 0.07 | 0.05 | 0.05 | 0.05 | 0.04 | 0.05 | |
| 1 | 0.17 | 0.15 | 0.14 | 0.13 | 0.12 | 0.09 | 0.07 | 0.05 | 0.05 | 0.05 | 0.05 | 0.05 | |
| 0.5 | 0.18 | 0.15 | 0.14 | 0.14 | 0.12 | 0.09 | 0.07 | 0.06 | 0.06 | 0.05 | 0.05 | 0.06 | |
| 0 | 0.18 | 0.15 | 0.15 | 0.13 | 0.12 | 0.08 | 0.07 | 0.06 | 0.06 | 0.06 | 0.06 | 0.06 | |

| Colistin \ Rifampicin | 256 | 128 | 64 | 32 | 16 | 8 | 4 | 2 | 1 | 0.5 | 0.25 | 0 | FIC index |
|---|---|---|---|---|---|---|---|---|---|---|---|---|---|
| 128 | 0.15 | 0.12 | 0.10 | 0.08 | 0.07 | 0.06 | 0.05 | 0.05 | 0.05 | 0.05 | 0.05 | 0.05 | 0.01758 |
| 64 | 0.13 | 0.11 | 0.10 | 0.08 | 0.07 | 0.06 | 0.05 | 0.05 | 0.04 | 0.05 | 0.16 | 0.26 | |
| 32 | 0.13 | 0.12 | 0.10 | 0.08 | 0.09 | 0.06 | 0.05 | 0.05 | 0.04 | 0.08 | 0.21 | 0.34 | |
| 16 | 0.12 | 0.12 | 0.10 | 0.08 | 0.07 | 0.06 | 0.05 | 0.05 | 0.04 | 0.10 | 0.13 | 0.32 | |
| 8 | 0.12 | 0.11 | 0.10 | 0.08 | 0.07 | 0.06 | 0.05 | 0.05 | 0.04 | 0.24 | 0.28 | 0.17 | |
| 4 | 0.12 | 0.12 | 0.10 | 0.08 | 0.07 | 0.06 | 0.05 | 0.14 | 0.26 | 0.27 | 0.27 | 0.32 | |
| 2 | 0.13 | 0.21 | 0.30 | 0.36 | 0.22 | 0.24 | 0.23 | 0.25 | 0.24 | 0.25 | 0.26 | 0.48 | |
| 0 | 0.56 | 0.54 | 0.53 | 0.52 | 0.49 | 0.50 | 0.52 | 0.51 | 0.51 | 0.51 | 0.50 | 0.57 | |

Figure 30

| Colistin \ Rifampicin | 32 | 16 | 8 | 4 | 2 | 1 | 0.5 | 0.25 | 0.125 | 0.0625 | 0.03125 | 0 | FIC index |
|---|---|---|---|---|---|---|---|---|---|---|---|---|---|
| 32 | 0.60 | 0.50 | 0.45 | 0.42 | 0.41 | 0.40 | 0.40 | 0.39 | 0.39 | 0.40 | 0.39 | 0.38 | 0.06183 |
| 16 | 0.59 | 0.50 | 0.45 | 0.43 | 0.41 | 0.41 | 0.40 | 0.40 | 0.40 | 0.41 | 0.40 | 0.40 | |
| 8 | 0.59 | 0.51 | 0.46 | 0.43 | 0.42 | 0.41 | 0.41 | 0.41 | 0.40 | 0.42 | 0.40 | 1.26 | |
| 4 | 0.59 | 0.51 | 0.45 | 0.43 | 0.42 | 0.42 | 0.41 | 0.41 | 0.40 | 0.40 | 0.40 | 1.27 | |
| 2 | 0.60 | 0.50 | 0.46 | 0.44 | 0.43 | 0.59 | 0.41 | 0.41 | 0.41 | 0.41 | 0.92 | 1.35 | |
| 1 | 0.59 | 0.52 | 0.47 | 0.44 | 0.43 | 0.42 | 0.42 | 1.35 | 0.41 | 1.42 | 1.33 | 1.47 | |
| 0.5 | 0.60 | 0.50 | 1.29 | 1.33 | 1.31 | 1.29 | 1.32 | 1.29 | 1.32 | 1.39 | 1.45 | 1.57 | |
| 0 | 0.71 | 0.82 | 0.88 | 1.28 | 1.40 | 1.46 | 1.46 | 1.45 | 1.51 | 1.48 | 1.48 | 1.57 | |

Figure 31

| MY0130002 \ MY0130001 | 1024 | 512 | 256 | 128 | 64 | 32 | 16 | 8 | 4 | 2 | 0 | MY0130001 |
|---|---|---|---|---|---|---|---|---|---|---|---|---|
| 32 | 0.19 | 0.18 | 0.15 | 0.13 | 0.11 | 0.08 | 0.07 | 0.06 | 0.05 | 0.05 | 0.05 | 0.05 | 0 |
| 16 | 0.16 | 0.15 | 0.14 | 0.13 | 0.12 | 0.09 | 0.06 | 0.05 | 0.05 | 0.05 | 0.04 | 0.04 |
| 8 | 0.16 | 0.15 | 0.14 | 0.13 | 0.11 | 0.08 | 0.07 | 0.06 | 0.05 | 0.05 | 0.04 | 0.13 |
| 4 | 0.16 | 0.15 | 0.14 | 0.13 | 0.11 | 0.08 | 0.06 | 0.05 | 0.05 | 0.05 | 0.04 | 0.28 |
| 2 | 0.17 | 0.14 | 0.14 | 0.13 | 0.11 | 0.09 | 0.06 | 0.05 | 0.05 | 0.05 | 0.05 | 0.46 |
| 1 | 0.17 | 0.14 | 0.14 | 0.14 | 0.11 | 0.09 | 0.28 | 0.30 | 0.36 | 0.42 | 0.43 | 0.61 |
| 0.5 | 0.17 | 0.15 | 0.28 | 0.41 | 0.46 | 0.49 | 0.51 | 0.48 | 0.48 | 0.50 | 0.52 | 0.58 |
| 0 | 0.16 | 0.40 | 0.43 | 0.66 | 0.70 | 0.73 | 0.73 | 0.73 | 0.74 | 0.59 | 0.66 | 0.73 |

ZIDOVUDINE COMBINATION THERAPIES FOR TREATING MICROBIAL INFECTIONS

CROSS REFERENCE TO RELATED APPLICATIONS

This application is a National Stage of International Application No. PCT/GB2015/050209, filed on Jan. 29, 2015, which claims priority from British Patent Application No. 1401617.4, filed on Jan. 30, 2014, the contents of all of which are incorporated herein by reference in their entirety.

TECHNICAL FIELD

The present invention relates to the use of an anti-retroviral agent for killing clinically latent microorganisms associated with microbial infections in combination with an anti-microbial agent.

BACKGROUND

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery,* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet,* 357, 1179 (2001) and *Lancet,* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

BRIEF DESCRIPTION OF THE DRAWINGS

FIG. 2a.

FIG. 5 is a table showing the results of a combination of rifampicin and colistin with no addition of HT0120663. The wells marked yellow demonstrate growth. Clear wells indicate growth inhibition or no growth.

FIG. 6 is a table showing the results of a combination of rifampicin and colistin with addition of HT0120663 at 0.5 µg/ml. The wells marked yellow demonstrate growth. Clear wells indicate growth inhibition or no growth.

FIG. 7 is a table showing the results of a combination of rifampicin and colistin with addition of HT0120663 at 1 µg/ml. The wells marked yellow demonstrate growth. Clear wells indicate growth inhibition or no growth.

FIG. 8 is a table showing the results of a combination of rifampicin and colistin with addition of HT0120663 at 2 µg/ml. The wells marked yellow demonstrate growth. Clear wells indicate growth inhibition or no growth.

FIG. 9 is a table showing the results of a combination of rifampicin and colistin with addition of HT0120663 at 4 µg/ml. The wells marked yellow demonstrate growth. Clear wells indicate growth inhibition or no Growth.

FIG. 10 is a table showing the results of a combination of rifampicin and colistin with addition of HT0120663 at 8 µg/ml. The wells marked yellow demonstrate growth. Clear wells indicate growth inhibition or no growth.

FIG. 11 is a table showing the results of a combination of rifampicin and colistin with addition of HT0120663 at 16 µg/ml. The wells marked yellow demonstrate growth. Clear wells indicate growth inhibition or no growth.

FIG. 12 is a table showing the results of a combination of rifampicin and colistin with no addition of HT0120663. The wells marked yellow demonstrate growth. Clear wells indicate growth inhibition or no growth.

FIG. 13 is a table showing the results of a combination of rifampicin and colistin with addition of HT0120663 at 0.125 µg/ml. The wells marked yellow demonstrate growth. Clear wells indicate growth inhibition or no growth.

FIG. 14 is a table showing the results of a combination of rifampicin and colistin with addition of HT0120663 at 0.25 µg/ml. The wells marked yellow demonstrate growth. Clear wells indicate growth inhibition or no growth.

FIG. 15 is a table showing the results of a combination of rifampicin and colistin with addition of HT0120663 at 0.5 µg/ml. The wells marked yellow demonstrate growth. Clear wells indicate growth inhibition or no growth.

FIG. 16 is a table showing the results of a combination of rifampicin and colistin with addition of HT0120663 at 1 µg/ml. The wells marked yellow demonstrate growth. Clear wells indicate growth inhibition or no growth.

FIG. 17 is a table showing the results of a combination of rifampicin and colistin with addition of HT0120663 at 2 µg/ml, The wells marked yellow demonstrate growth. Clear wells indicate growth inhibition or no growth.

FIG. 18 is a table showing the results of a combination of rifampicin and colistin with addition of HT0120663 at 4 µg/ml. The wells marked yellow demonstrate growth. Clear wells indicate growth inhibition or no growth.

FIG. 19 is a table showing the results of a combination of rifampicin and colistin with addition of HT0120663 at 3 µg/ml. Clear wells indicate growth inhibition or no growth.

FIG. 20 is a table showing the results of a combination of rifampicin and colistin with addition of HT0120663 at 16 μg/ml, Clear wells indicate growth inhibition or no growth.

FIG. 21 is a table showing the results of a combination of rifampicin and colistin with addition of HT0120663 at 32 μg/ml. Clear wells indicate growth inhibition or no growth.

FIG. 22 is a table showing the results of a combination of rifampicin and colistin with no addition of HT0120663 against *E. coli* NDM-1 2471. The wells marked yellow demonstrate growth. Clear wells indicate growth inhibition or no growth.

FIG. 23 is a table showing the results of a combination of rifampicin and colistin with addition of HT0120663 at 0.5 μg/ml against *E. coli* NDM-1 2471. The wells marked yellow demonstrate growth. Clear wells indicate growth inhibition or no growth, FIG. 24 is a table showing the results of a combination of rifampicin and colistin with addition of HT0120663 at 1 μg/ml against *E. coli* NDM-1 2471. The wells marked yellow demonstrate growth. Clear wells indicate growth inhibition or no growth.

FIG. 25 is a table showing the results of a combination of rifampicin and colistin with addition of HT0120663 at 2 μg/ml against *E. coli* NDM-1 2471. The wells marked yellow demonstrate growth. Clear wells indicate growth inhibition or no growth.

FIG. 26 is a table showing the results of a combination of rifampicin and colistin with addition of HT0120663 at 4 μg/ml against *E. coil* NDM-1 2471. The wells marked yellow demonstrate growth. Clear wells indicate growth inhibition or no growth.

FIG. 27 is a table showing the results of a combination of rifampicin and colistin with addition of HT0120663 at 8 μg/ml. The wells marked yellow demonstrate growth. Clear wells indicate growth inhibition or no growth.

FIG. 28 is a table showing the results of a combination of rifampicin and colistin with addition of HT0120663 at 16 μg/ml. The wells marked yellow demonstrate growth. Clear wells indicate growth inhibition or no growth.

FIG. 29 is a chequerboard showing synergy between colistin and rifampicin against NDM-1 *Klebsiella pneumonia*.

FIG. 30 is a chequerboard showing synergy between colistin and rifampicin against NDM-1 *E. coli*.

Figures 32, 33, 34, 35:
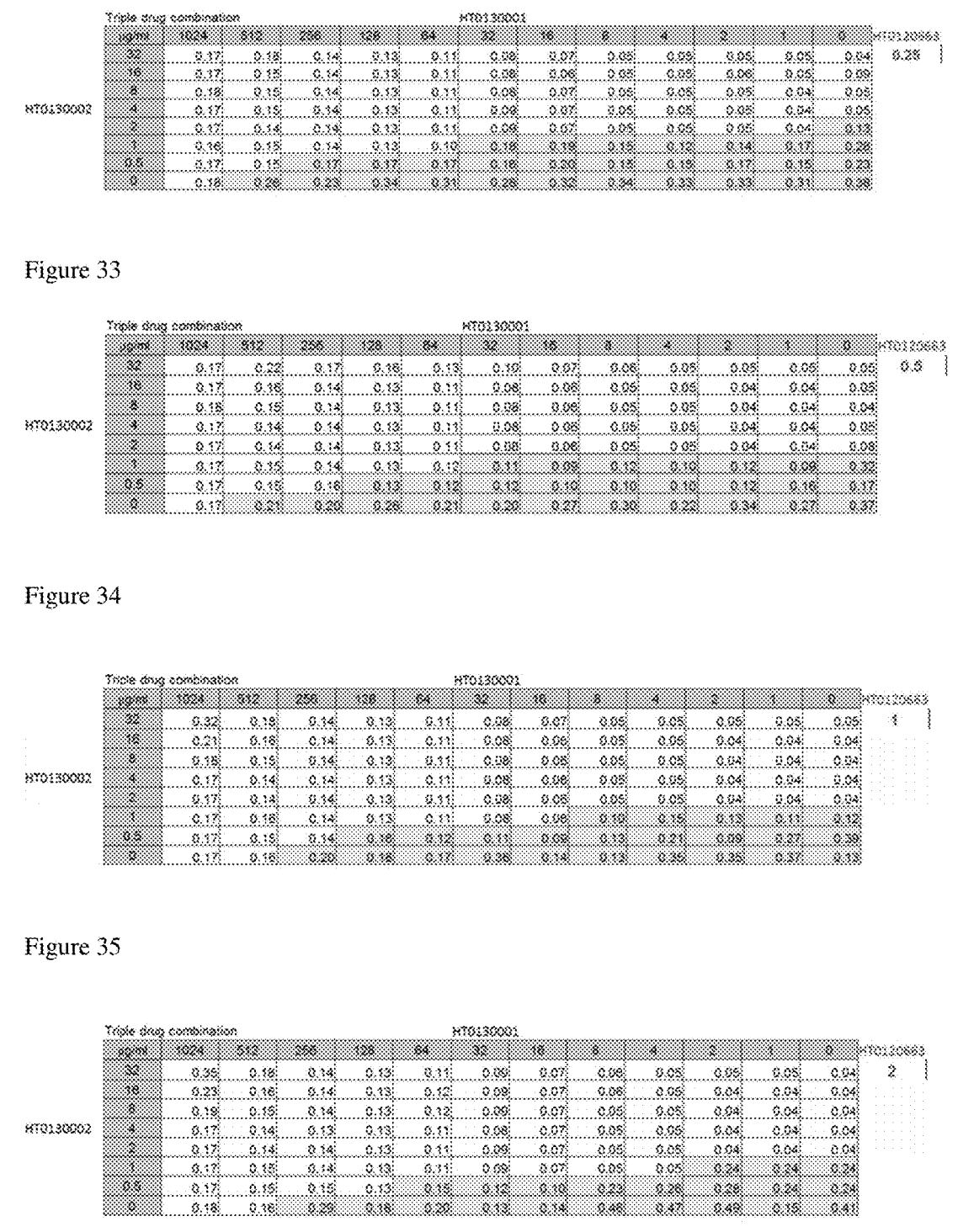
Figures 36, 37, 38, 39:
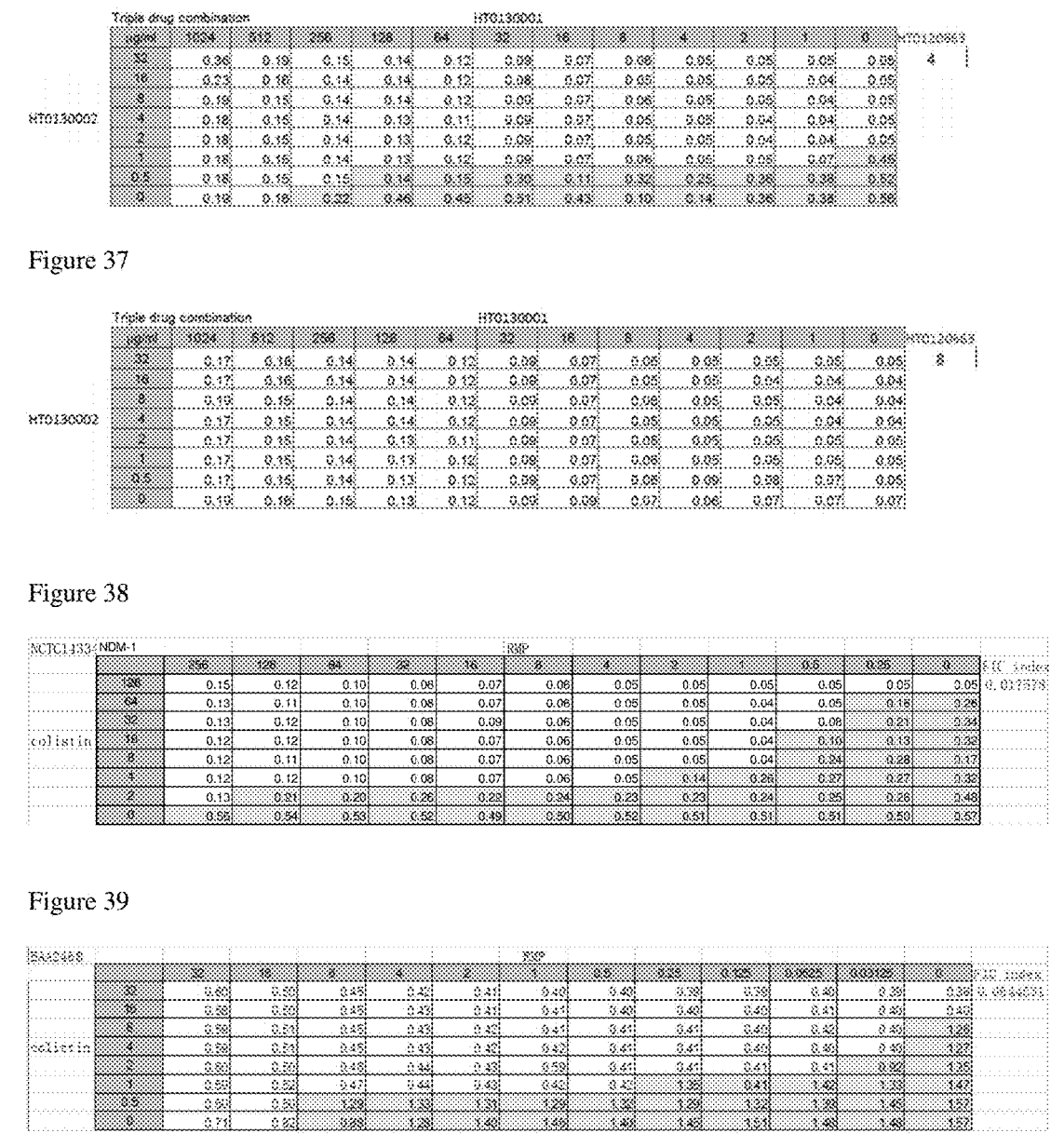

FIGS. 31 to 37 are each a chequerboard showing synergy between colistin, rifampicin and HT0120663 against NDM-1 *Klebsiella pneumonia* as described in Example 1.

Figures 40, 41, 42, 43:
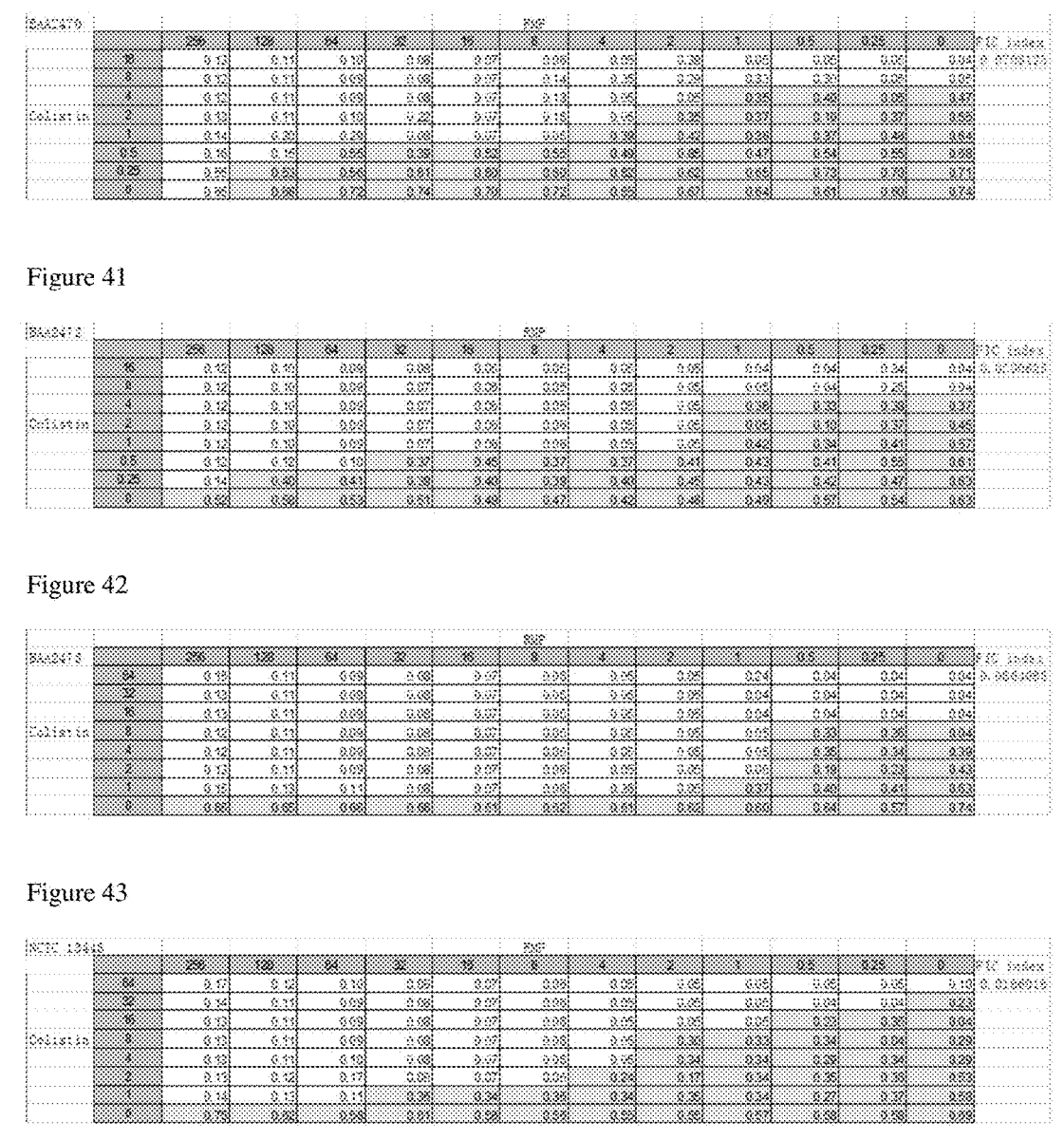

FIGS. 38 to 43 are each a chequerboard showing synergy between rifampicin and colistin against log phase gram negative bacteria as described in Example 5.

DETAILED DESCRIPTION

Figure 1A:
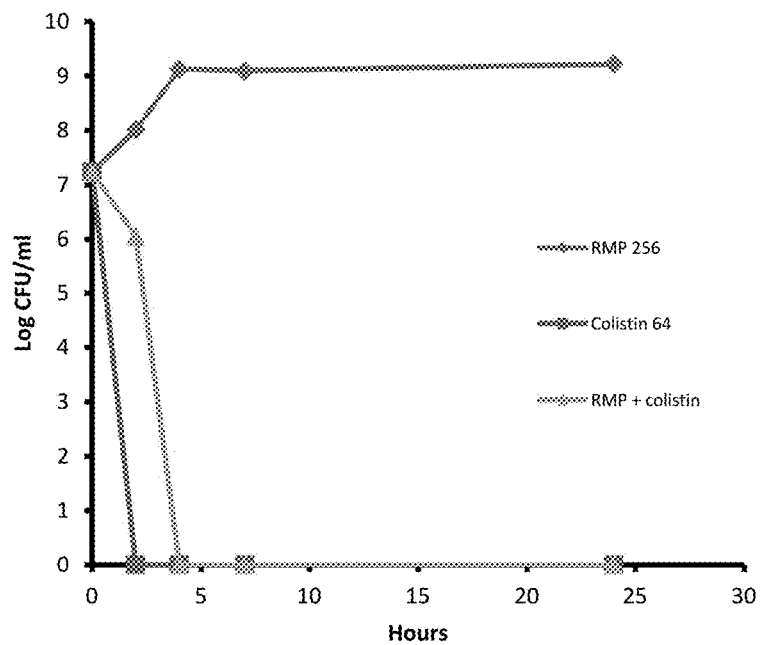
FIG. 1a, FIG. 1b, and FIG. 1c are time kill curves showing the effect of the combination of colistin and rifampicin against NDM-1 *Klebsiella pneumonia* compared to colistin and rifampicin singly.
Figure 1B:
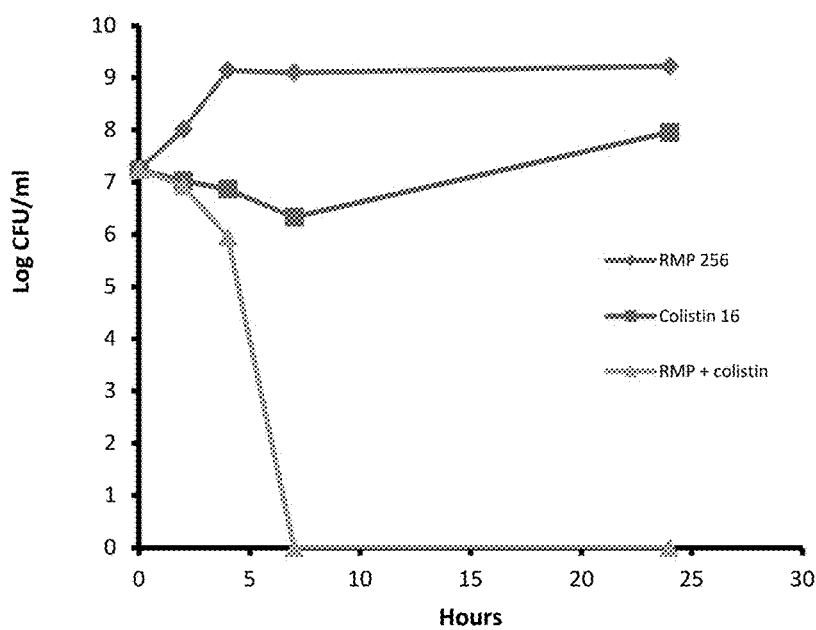
Figure 1C:
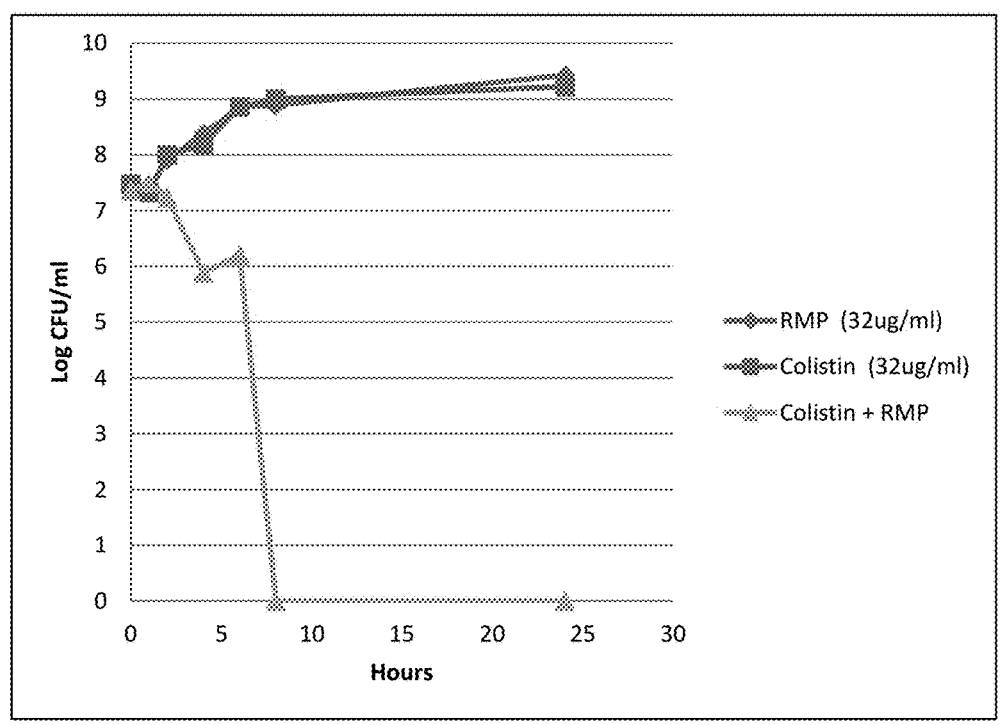
Figure 2A:
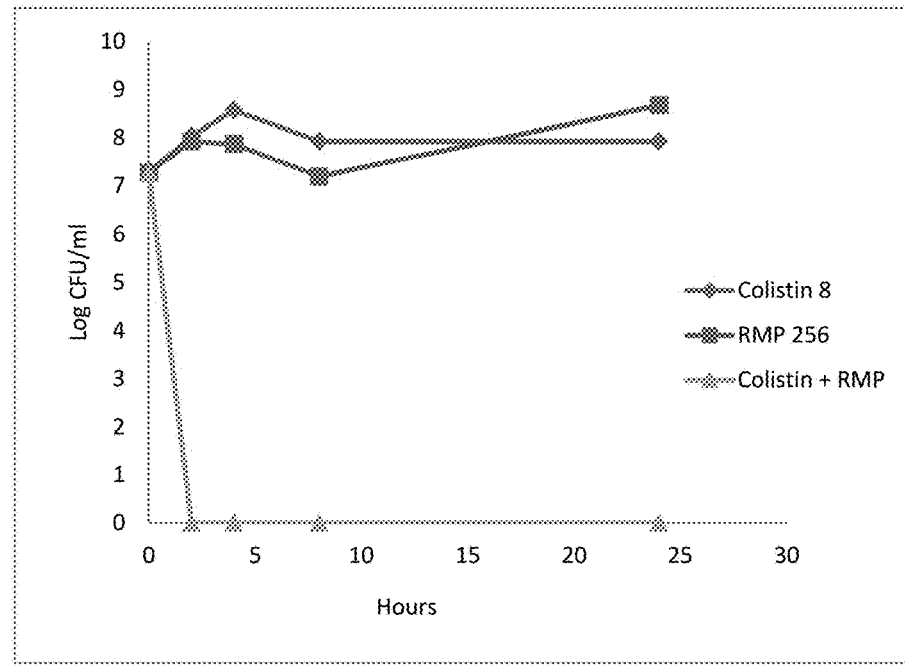
Figure 2B:
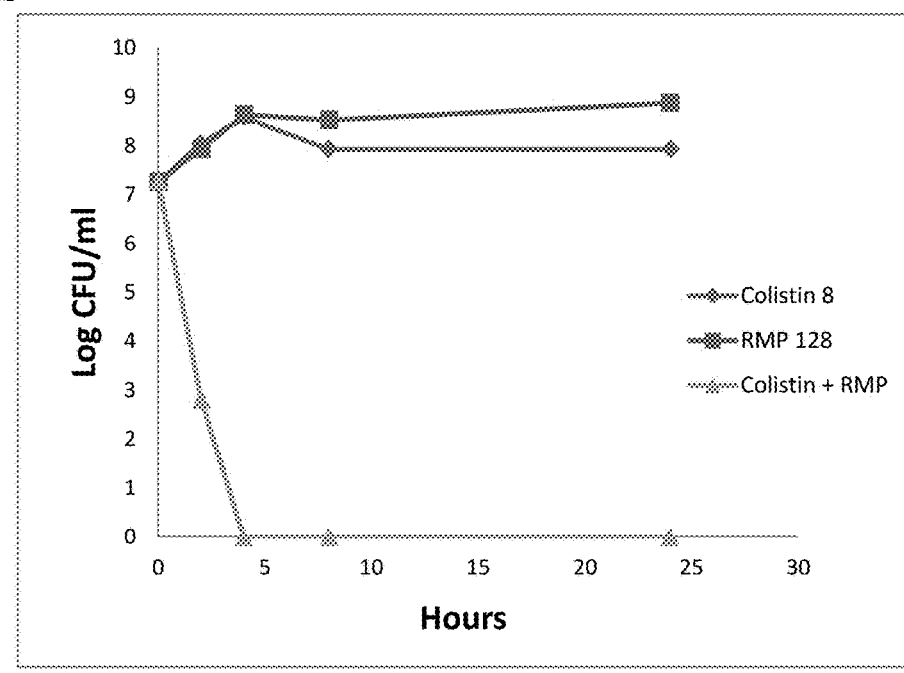
FIG. 2b.
Figure 2C:
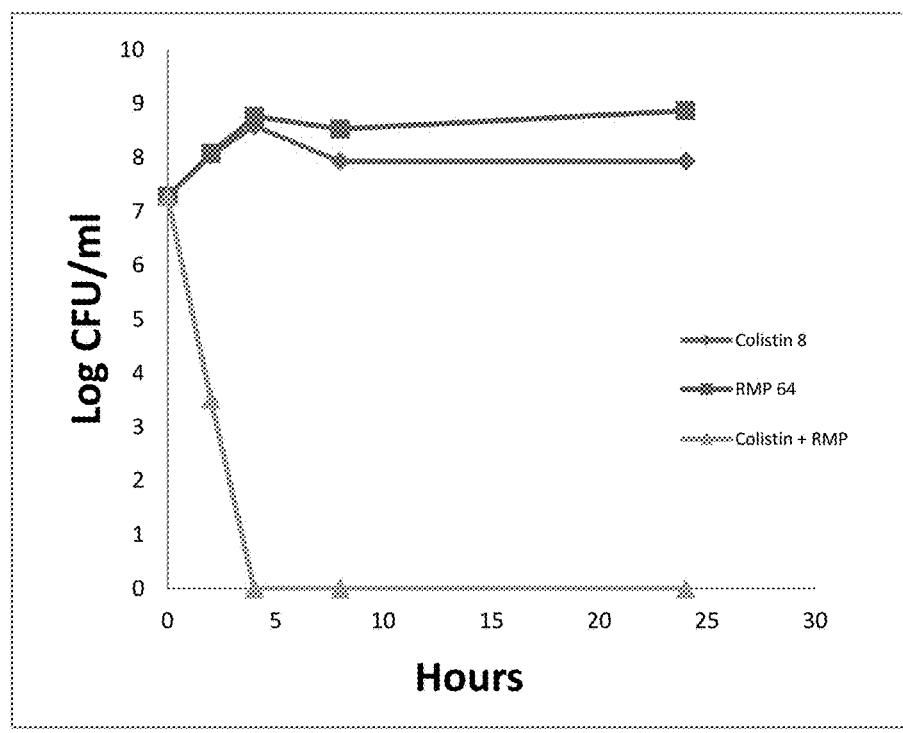
FIG. 2c, and FIG. 2d are time kill curves showing the effect of the combination of colistin and rifampicin against NDM-1 *E. coil* compared to colistin and rifampicin singly.
Figure 2D:
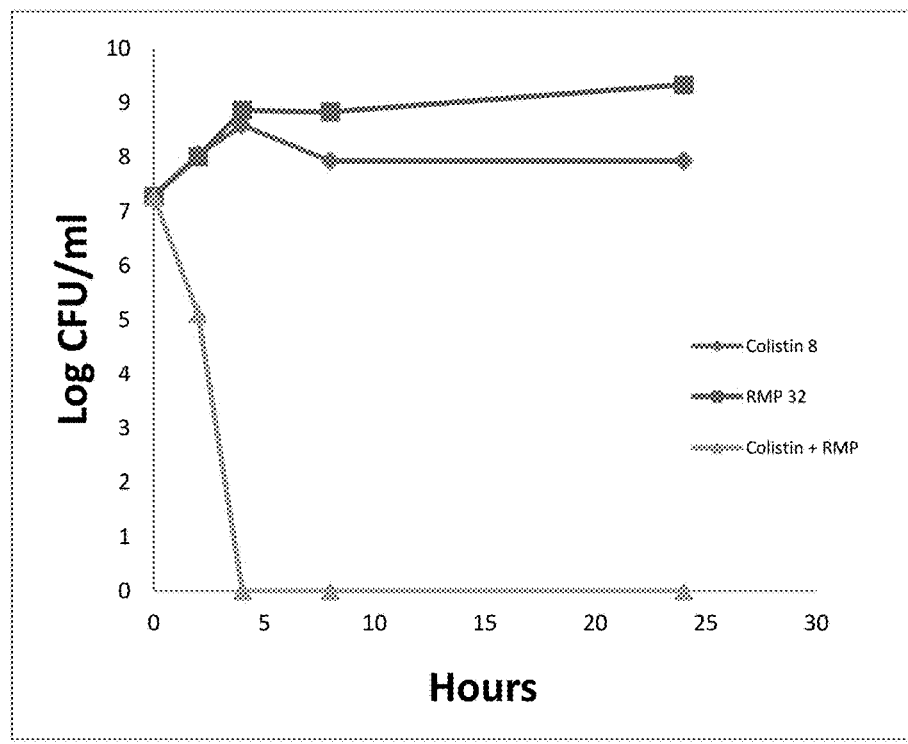

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science*, 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.*, 4, 395-404 (1988); *J. Med. Microbiol.*, 38, 197-202 (1993); *J. Bacteriol.*, 182, 1794-1801 (2000); ibid. 182, 6358-6365 (2000); ibid. 183, 6746-6751 (2001); *FEMS Microbiol. Lett.*, 202, 59-65 (2001); and *Trends in Microbiology*, 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad.*

*Sci. USA*, 92, 11736-11740 (1995); *J. Bacteriol.*, 179, 6688-6691 (1997); and *Antimicrob. Agents Chemother.*, 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

The following articles disclose use of colistin, a polymixin, and rifampicin as combination therapy for bacterial infections such as multidrug resistant (MDR) *Acinetobacter baumannii*, (Motaouakkil S et al J Infect (2006) 53 274-278, Bassetti M et al J Antimicrob Chemo (2008) 61 417-420, Zhou A et al The AAPS J published online on 16 Oct. 2013 DOI:10.1208/s12248-013-9537-8). Lee J J et al (Antimicrob Agents & Chemo (2013) 57(8) 3738-3745) disclose the results of using a combination of colistin and rifampicin in an in vitro model of MDR-*A. baumannii*. Synergy was observed at come concentrations over some time periods. A mechanism is proposed whereby colistin not only self-promotes its own entry into the bacteria but thereby increases the penetration by rifampicin.

Reporting on a multicentre, randomized clinical trial Durante-Mangoni E et al Clin Infec Dis (2013) 57(3) 349-58 conclude that due to there being no reduction in 30-day mortality in the combination group, "These results indicate that, at present, rifampicin should not be routinely combined with colistin in clinical practice. The increased rate of *A baumannii* eradication with combination treatment could still imply a clinical benefit."

Tascini C et al (Antimicrob Agents & Chemo (2013) 57(8) 3990-3993 disclose the use of the same combination in carbapenem-resistant *Klebsiella pneumoniae*. On the basis of the favourable synergistic effect, the use of the combination in MDR-*K pneumonia* is proposed as having a clinical role.

Recently, there has been report of an anti-retroviral drug, zidovudine being active as an anti-microbial when combined with gentamicin. Thus, Doléans-Jordheim A. et al., disclosed (Eur J Clin Microbiol Infect Dis. 2011 October; 30(10):1249-56) that Zidovudine (AZT) had a bactericidal effect on some enterobacteria, yet could induce resistance in *Escherichia coli*. These resistances were associated with various modifications in the thymidine kinase gene. Furthermore, an additive or synergistic activity between AZT and the two aminoglycoside antibiotics amikacin and gentamicin was observed against enterobacteria.

Accordingly, in one embodiment of the present invention there is provided the use of zidovudine in combination with; a polymyxin selected from colistin or polymyxin B; an anti-tuberculosis antibiotic selected from rifampicin, rifapentine or rifabutin; and optionally piperine, for treating a microbial infection.

In a further embodiment the invention relates to a product comprising zidovudine in combination with; a polymyxin selected from colistin and polymyxin B; an anti-tuberculosis antibiotic selected from rifampicin, rifapentine or rifabutin; and optionally piperine, as a combined preparation for simultaneous, separate or sequential use in killing clinically latent microorganisms associated with a microbial infection.

An additional embodiment of the invention relates to a pharmaceutical composition comprising zidovudine in combination with; a polymyxin selected from colistin and polymyxin B; an anti-tuberculosis antibiotic selected from rifampicin, rifapentine or rifabutin; and optionally piperine, and a pharmaceutically acceptable carrier for use in treating a microbial infection, preferably killing clinically latent microorganisms associated with a microbial infection.

In each described embodiment, the preferred anti-tuberculosis antibiotic is rifampicin.

The present invention therefore further relates to a composition comprising zidovudine, colistin and rifampicin for simultaneous, separate or sequential use in treating a microbial infection.

The present invention therefore also includes;

The use of zidovudine for the treatment of a microbial infection in combination with colistin and rifampicin or rifapentine, The use of colistin for the treatment of a microbial infection in combination with zidovudine and rifampicin or rifapentine, and, The use of rifampicin or rifapentine for the treatment of a microbial infection in combination with colistin and zidovudine.

In each embodiment of the present invention the addition of piperine is optional. On the basis of data regarding piperine as an inhibitor of both human P-glycoprotein and CYP3A4 described in inter alia, J Pharmacol Exp Ther (2002) 302(2) 645-650 the activity of piperine is believed to be beneficial to the combinations defined herein. Thus, in a preferred embodiment, piperine is included in the combinations of the present invention.

The present invention is also based upon the unexpected finding that the activity of the combinations of a polymyxin selected from colistin and polymyxin B; and an anti-tuberculosis antibiotic selected from rifampicin, rifapentine or rifabutin, is substantially improved when administered with zidovudine. Moreover, the combinations have surprisingly been shown to exhibit synergistic antimicrobial activity against log phase (i.e. multiplying) and/or clinically latent microorganisms. The surprising biological activity of the combinations of the present invention offers the opportunity to shorten chemotherapy regimes and may result in a reduction in the emergence of microbial resistance.

As described below, the combination of the present invention has been demonstrated to be particularly effective against drug-resistant bacteria opening the way for said combinations to be administered both to drug-resistant strains and in said strains before drug-resistance is built up i.e. as a first line treatment.

The combinations of the present invention have in particular been demonstrated to be effective against Gram-negative bacteria, specifically drug-resistant Gram-negative bacteria.

As used herein, the term "in combination with" covers both separate and sequential administration of an antimicrobial agent and an anesthetic agent. When the agents are administered sequentially, either agent may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

The combinations of the present invention may be used to treat microbial infections. In particular they may be used to kill multiplying and/or clinically latent microorganisms associated with microbial infections. References herein to the treatment of a microbial infection therefore include killing multiplying and/or clinically latent microorganisms associated with such infections. Preferably, the combinations of the present invention are used to kill clinically latent microorganisms associated with microbial infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or
(II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

As summarised above, Doléans-Jordheim A. et al., disclosed (Eur J Clin Microbiol Infect Dis. 2011 October; 30(10):1249-56) that zidovudine (AZT) had a bactericidal effect on some enterobacteria, in particular in combination with amikacin and gentamicin.

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g. beta-haemolytic, pyogenic streptococci (such as *Strept. agalactiae, Strept. canis, StrepL dysgalactiae dysgalactiae, Strept. dysgalactiae equisimilis, Strept equi equi, Strept equi zooepidemicus, Strept. iniae, Strept porcinus* and *Strept pyogenes*), microaerophilic, pyogenic streptococci (*Streptococcus* "milleri", such as *Strept. anginosus, Strept constellatus constellatus, Strept constellatus pharyngidis* and *Strept intermedius*), oral streptococci of the "mitis" (alpha-haemolytic—*Streptococcus* "viridans", such as *Strept. mitis, Strept. oralis, Strept. sanguinis, Strept. cristatus, Strept gordonfi* and *Strept. parasanguinis*), "salivarius" (non-haemolytic, such as *Strept. salivarius* and *Strept vestibularis*) and "mutans" (tooth-surface streptococci, such as *Strept. criceti, Strept. mutans, Strept ratti* and *Strept sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri;*

Bacillaceae, such as *Bacillus anthracis, Bacillus subtilis, Bacillus thuringiensis, Bacillus stearothermophilus* and *Bacillus cereus;*

Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr.* vulgaris), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. Iwoffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*); *Bacteroides fragilis;*

*Peptococcus* (e.g. *Peptococcus niger*);

*Peptostreptococcus;*

*Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. male-*

*nominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);

Mycoplasma (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

Haemophilus (e.g. *Haemophilus influenzae, Haemophilus ducreyi, Haemophilus aegyptius, Haemophilus parainfluenzae, Haemophilus haemolyticus* and *Haemophilus parahaemolyticus*);

Actinobacillus (e.g. *Actinobacillus actinomycetemcomitans, Actinobacillus equuli, Actinobacillus hominis, Actinobacillus lignieresii, Actinobacillus suis* and *Actinobacillus ureae*);

Actinomyces (e.g. *Actinomyces israelii*);

Brucella (e.g. *Brucella abortus, Brucella canis, Brucella melintensis* and *Brucella suis*);

Campylobacter (e.g. *Campylobacter jejuni, Campylobacter coli, Campylobacter lari* and *Campylobacter fetus*);

*Listeria monocytogenes*;

Vibrio (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae*;

Corynebacteriaceae (e.g. *Corynebacterium diphtheriae, Corynebacterium jeikeum* and *Corynebacterium urealyticum*);

Spirochaetaceae, such as Borrelia (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and Treponema (*Treponema pallidum* ssp. *pallidum, Treponema pallidum* ssp. *endemicum, Treponema pallidum* ssp. *pertenue* and *Treponema carateum*);

Pasteurella (e.g. *Pasteurella aerogenes, Pasteurella bettyae, Pasteurella canis, Pasteurella dagmatis, Pasteurella gaffinarum, Pasteurella haemolytica, Pasteurella multocida multocida, Pasteurella multocida gallicida, Pasteurella multocida septica, Pasteurella pneumotropica* and *Pasteurella stomatis*);

Bordetella (e.g. *Bordetella bronchiseptica, Bordetella hinzii, Bordetella holmseii, Bordetella parapertussis, Bordetella pertussis* and *Bordetella trematum*);

Nocardiaceae, such as Nocardia (e.g. *Nocardia asteroides* and *Nocardia brasiliensis*); Rickettsia (e.g. *Ricksettsii* or *Coxiella burnetii*);

Legionella (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*);

*Moraxella catarrhalis*;

*Cyclospora cayetanensis*;

*Entamoeba histolytica*;

*Giardia lamblia*;

*Trichomonas vaginalis*;

*Toxoplasma gondii*;

*Stenotrophomonas maltophilia*;

*Burkholderia cepacia; Burkholderia mallei* and *Burkholderia pseudomallei*;

*Francisella tularensis*;

Gardnerella (e.g. *Gardneralla vaginalis* and *Gardneralla mobiluncus*);

*Streptobacillus moniliformis*;

Flavobacteriaceae, such as Capnocytophaga (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

Bartonella (*Bartonella bacilliformis, Bartonella clarridgeiae, Bartonella elizabethae, Bartonella henselae, Bartonella quintana* and *Bartonella vinsonfi arupensis*);

Leptospira (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

Spirillium (e.g. *Spirillum minus*);

Baceteroides (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

Prevotella (e.g. *Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschfi, Prevotella melaninogenica, Prevotella nigrescens, Prevotella oralis, Prevotella oris, Prevotella oulora, Prevotella tannerae, Prevotella venoralis* and *Prevotella zoogleoformans*);

Porphyromonas (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis,*

*Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Cryptosporidium* (e.g. *C. parvum, C. hominis, C. canis, C. felis, C. meleagridis* and *C. muris*);

*Chlamydophila* (e.g. *Chlamydophila abortus (Chlamydia psittaci), Chlamydophila pneumoniae (Chlamydia pneumoniae)* and *Chlamydophila psittaci (Chlamydia psittaci)*);

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

Preferably, the bacterial infections treated by the combinations described herein are gram-negative infections. Particular bacteria that may be treated using a combination of the invention include:

Gram positive bacteria;

Staphylococci, such as *Staph. aureus* (either Methicillin-sensitive (i.e. MSSA) or Methicillin-resistant (i.e. MRSA)) and *Staph. epidermidis;*

Streptococci, such as *Strept. agalactiae* and *Strept. pyogenes;*

Bacillaceae, such as *Bacillus anthracis;*

Enterococci, such as *Enterococcus faecalis* and *Enterococcus faecium*; and

Gram negative bacteria;

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*); *Haemophilis influenzae;*

Mycobacteria, such as *Mycobacterium tuberculosis.*

Preferably, the bacterium is Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr.* vulgaris). The combination of the present invention is particularly beneficial in treating (multi)-drug-resistant ((M)DR) bacteria. With respect to Enterobacteriaceae, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebs. Pneumonia*.

It should be kept in mind that although a combination such as that claimed may initially be demonstrated to be functional in treating (M)DR strains, they can then be used in treating non-resistant strains. This is especially valuable in the context of the presently claimed combination where the primary therapy for Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*) are anti-microbial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

The combinations of the present invention may be used to treat infections associated with any of the above-mentioned bacterial organisms, and in particular they may be used for killing multiplying and/or clinically latent microorganisms associated with such an infection.

Particular conditions which may be treated using the combination of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, nephritis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, urinary tract infections, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* and *Enterococcus faecium*. In particular, the combination in kidney stone associated infections and catheter-associated infections arising from any of the bacteria described.

In a particular embodiment, the infection is selected from urinary tract infections (cystitis, nephritis, kidney stone associated infections and catheter-associated infections.

It will be appreciated that references herein to "treatment" extend to prophylaxis as well as the treatment of established diseases or symptoms.

Further preferred antimicrobial compounds for use in the present invention are those capable of killing clinically latent microorganisms. Methods for determining activity against clinically latent bacteria include a determination, under conditions known to those skilled in the art (such as those described in *Nature Reviews, Drug Discovery*, 1, 895-910 (2002), the disclosures of which are hereby incorporated by reference), of Minimum Stationary-cidal Concentration ("MSC") or Minimum Dormicidal Concentration ("MDC") for a test compound. A suitable compound screening method against clinically latent microorganisms is described in WO2000028074, the contents of which are incorporated herein by reference as if the publication was specifically and fully set forth herein.

As used herein the term "pharmaceutically acceptable derivative" means:
(a) pharmaceutically acceptable salts with either acids or bases (e.g. acid addition salts); and/or
(b) solvates (including hydrates).

Acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalenesulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient. In a preferred embodiment, the composition (administered alone or separately) is administered systemically eg intravenously, intramuscularly, via a catheter or inhaled.

Preferably, the compositions of the invention are formulated for oral or topical administration. In a preferred embodiment, the composition is a cream or an ointment adapted for nasal administration, in particular for delivery to the anterior nares.

The formulations may conveniently be presented in unit dosage form and may be prepared by any of the methods well known in the art of pharmacy e.g. as described in "*Remington: The Science and Practice of Pharmacy*", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci, Streptococci, Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczma, burns, abrasions and skin wounds.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

Suitable dosages and formulations for the administration of colistin are described in the product label for Colomycin® which can be found at http://www.medicines.org.uk/emc/medicine/6301/SPC/Colomycin+Tablets/

Suitable dosages and formulations for the administration of rifampicin are described in the product label for Rifadin® capsules which can be found at http://www.medicines.org.uk/emc/medicine/21223/SPC/Rifadin+300 mg+Capsules/ or Rifadin® for Infusion which can be found at http://www.medicines.org.uk/emc/medicine/6435/SPC/Rifadin+For+Infusion+600 mg/

Suitable dosages and formulations for the administration of rifapentine are described in the product label for Priftin®. The preferred dosing regimen for the treatment of tuberculosis caused by drug-susceptible organisms as part of regimens consisting of an initial 2 month phase followed by a 4 month continuation phase. The Initial Phase (2 Months) involves administration of 600 mg twice weekly for two months by direct observation of therapy, with an interval of no less than 3 consecutive days (72 hours) between doses, in combination with other antituberculosis drugs. The Continuation Phase (4 Months) involves administration of 600 mg once weekly for 4 months by direct observation therapy with isoniazid or another appropriate antituberculous agent.

Suitable dosages and formulations for the administration of zidovudine are described in the product label for Retrovir® oral solution or capsules which can be found at http://www.medicines.org.uk/emc/medicine/12444/SPC/Retrovir+250 mg+Capsules/

The administration of the combination of the invention by means of a single patient pack, or patient packs of each composition, including a package insert directing the patient to the correct use of the invention is a desirable feature of this invention.

The individual components of the combination of the invention may be administered simultaneously, separately or sequentially use. The administering physician will be able to decide whether to utilise the known dosing regimen and whether to maintain the simultaneous administration. For example, the daily administration of zidovudine and 8-hourly colistin may be superimposed on the regimen for administering rifapentine or rifampicin, particularly rifampicin.

According to a further embodiment of the present invention there is provided a patient pack comprising at least one active ingredient of the combination according to the invention and an information insert containing directions on the use of the combination of the invention.

In another embodiment of the invention, there is provided a double pack comprising in association for separate administration, an antimicrobial agent, preferably having biological activity against clinically latent microorganisms, and an anesthetic agent, preferably having biological activity against clinically latent microorganisms.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in Nature Reviews, Drug Discovery 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationery phase;

(2) treating the stationery phase culture with one or more antimicrobial agents at a concentration and or time sufficient to kill growing bacteria, thereby selecting a phenotypically resistant sub-population;

(3) incubating a sample of the phenotypically resistant subpopulation with one or more test compounds or agents; and (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

The chequerboard and Time kill experiments are described below and in Antimicrob Chemo (2013) 68, 374-384.

Example 1; In Vitro Synergy Effect of Colistin, Rifampicin and HT0120663 (Zidovudine) Against Log Phase NDM-1 *Klebsiella pneumonia* BAA2471 by Three Dimensional Chequerboard Method Objectives To test the synergy effect of colistin, rifampicin and HT0120663 (zidovudine) against log phase NDM-1 *Klebsiella pneumonia* BAA2472 by chequerboard method Materials and Methods 1. Bacterial strain used: NDM-1 BAA-2472TM, *Klebsiella pneumoniae* was obtained from the American Type Culture Collection.

2. Growth of bacteria: Log phase growth of BA2472 was carried out according to SOP R-005-00 Log Phase Growth of Bacteria 3. Antibiotics and preparation.

RMP was obtained from Sigma and was dissolved in DMSO to the stock concentration of 10 mg/ml.

Colistin was obtained from Sigma (10 mg/ml).

HT0120663 was obtained from Sigma and was dissolved in DMSO to make stock solution (10 mg/ml).

4. Chequerboard method

Rifampicin and colistin were combined using a two-dimensional chequerboard with two-fold dilutions of each drug starting concentration 8 μg/ml for rifampicin and 4 μg/ml for colistin. The triple combinations (Colistin/rifampicin/HT0120663) were tested by a three-dimensional chequerboard method where HT0120663 was added at a single concentration on each plate at 0.5, 1, 2, 4, 8, 16 μg/ml, respectively.

The overnight culture was diluted with nutrient broth (Oxoid) to $10^5$ CFU/ml and 280 μl of the culture suspension was added to each well to make the final volume of 300 μl.

5. Incubation of the compounds with the bacterial suspension was carried out for 24 hours.

6. The effects of combination were examined by calculating the fractional inhibitory concentration index (FICI) of double combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0.

Results

Figures 5, 6, 7, 8:
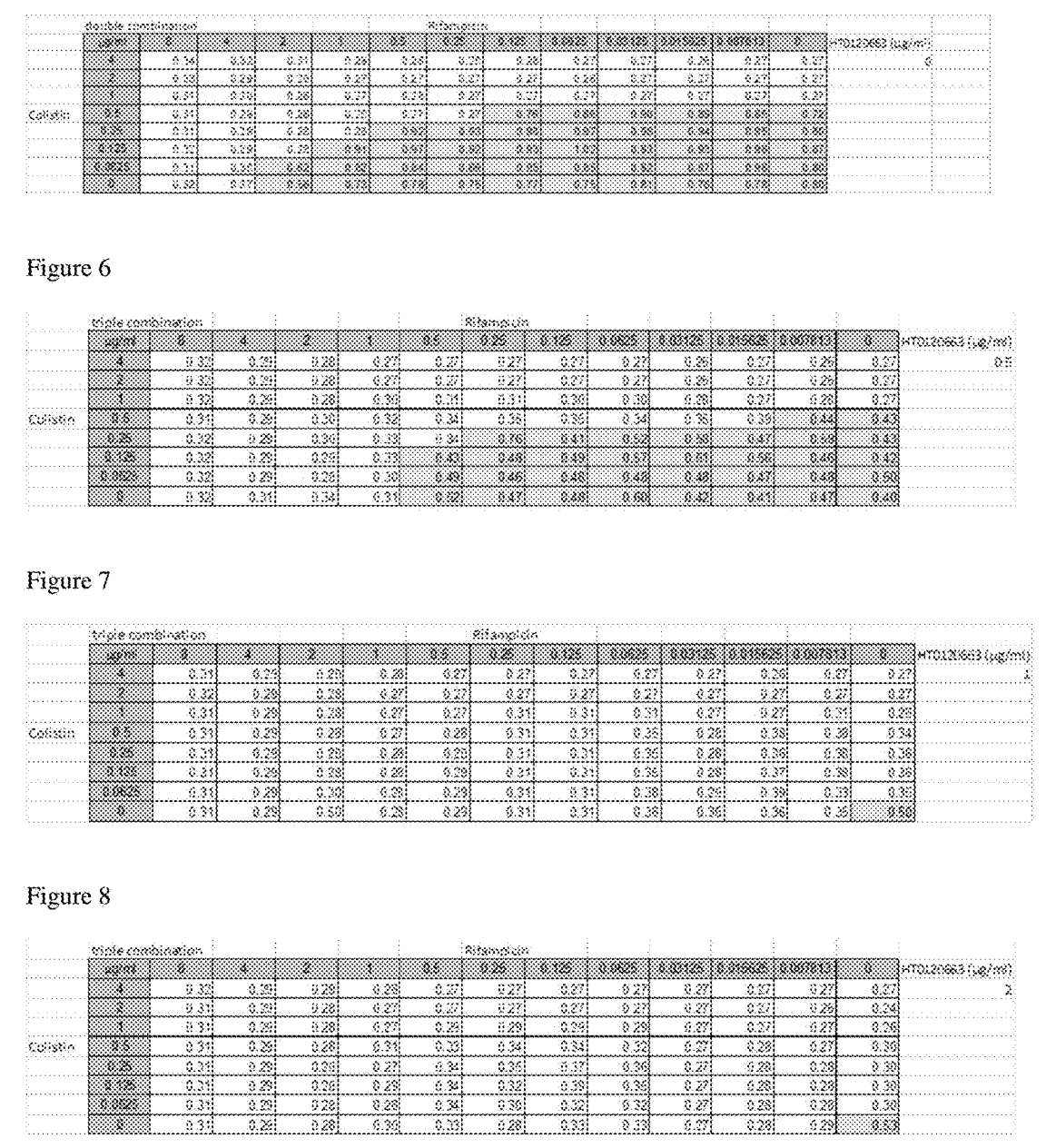

Combination of rifampicin and colistin with no addition of HT0120663. The wells marked yellow in FIG. 5 demonstrate growth. Clear wells indicate growth inhibition or no growth.

MIC of rifampicin was 4 μg/ml. In combination with 0.5 μg/ml of colistin, MIC reduced to 0.25 μg/ml. Colistin MIC was 1 μg/ml. In combination with 2 μg/ml of rifampicin, MIC reduced to 0.125 μg/ml. The FIC index is 0.188

Combination of rifampicin and colistin with addition of HT0120663 at 0.5 μg/ml. The wells marked yellow in FIG. 6 demonstrate growth. Clear wells indicate growth inhibition or no growth.

Addition of HT0120663 at 0.5 μg/ml in rifampicin and colistin combination reduced the MIC of rifampicin from 4 to 1 μg/ml which increased inhibition of growth.

Combination of rifampicin and colistin with addition of HT0120663 at 1 μg/ml. The wells marked yellow in FIG. 7 demonstrate growth. Clear wells indicate growth inhibition or no growth.

Combination of rifampicin and colistin with addition of HT0120663 at 2 µg/ml. The wells marked yellow in FIG. 8 demonstrate growth. Clear wells indicate growth inhibition or no growth.

Figures 9, 10, 11, 12:
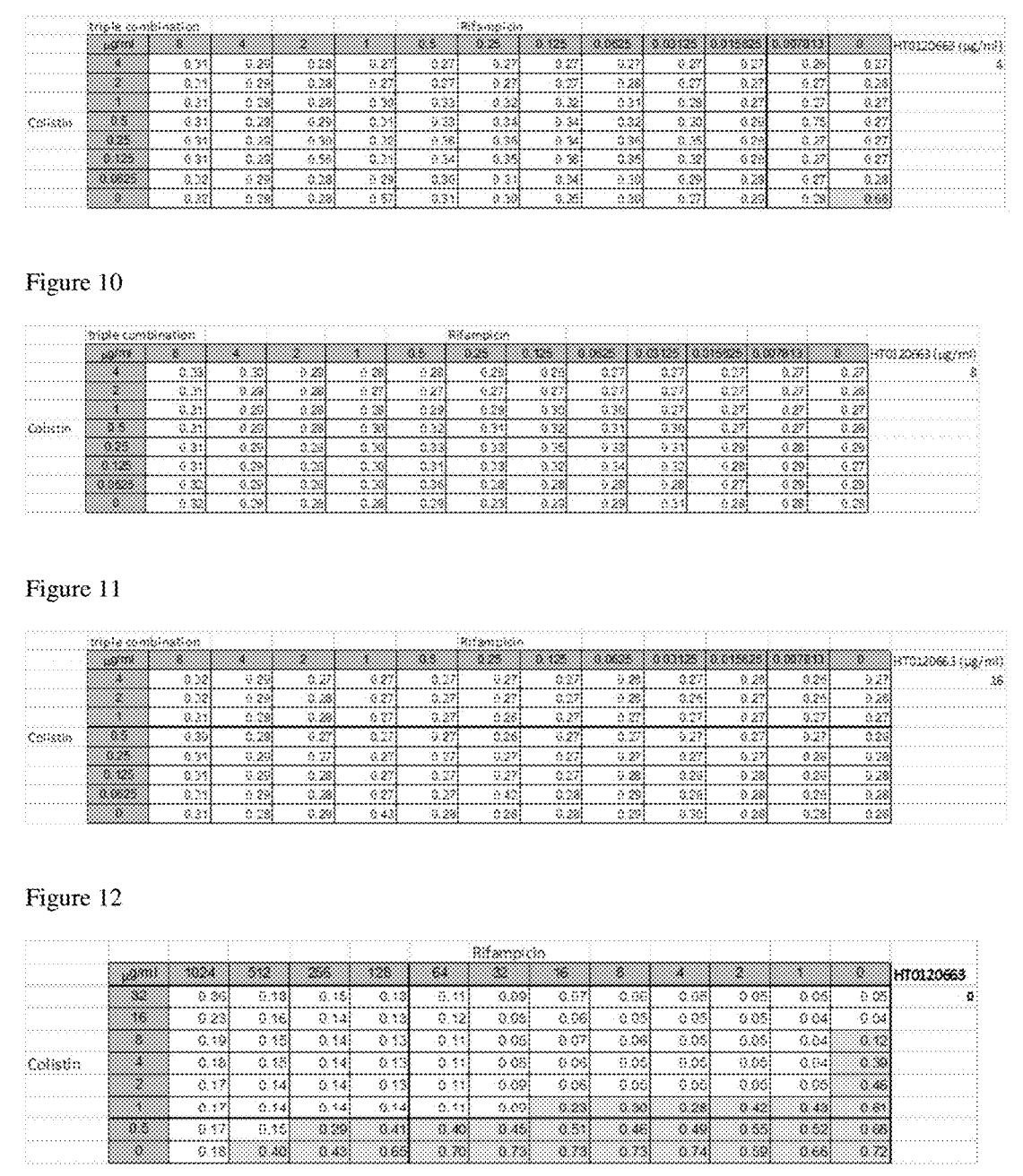

Combination of rifampicin and colistin with addition of HT0120663 at 4 µg/ml. The wells marked yellow in FIG. 9 demonstrate growth. Clear wells indicate growth inhibition or no growth.

Comparing with rifampicin and colistin combination, addition of HT0120663 at 1, 2 and 4 µg/ml inhibited all the growth except the last well where no drugs were present showing a synergistic triple combination effect.

Combination of rifampicin and colistin with addition of HT0120663 at 8 µg/ml. The wells marked yellow in FIG. 10 demonstrate growth. Clear wells indicate growth inhibition or no growth.

Combination of rifampicin and colistin with addition of HT0120663 at 16 µg/ml. The wells marked yellow in FIG. 11 demonstrate growth. Clear wells indicate growth inhibition or no growth.

When HT0120663 was increased to 8 µg/ml or above, complete inhibition of growth was seen. This was due to the MIC of HT0120663 (8 µg/ml) which on its own inhibited the bacterial growth.

Summary and Conclusion

This data show that three drug combination increased potency of each drug by reduction of MIC. Complete growth inhibition was seen when HT0120663 was added at 8 µg/ml or above.

Example 2: In Vitro Synergy Effect of Colistin, Rifampicin and HT0120663 (Zidovudine) Against Log Phase NDM-1 *Klebsiella pneumonia* BAA2473 by Chequerboard Method Objectives To test the synergy effect of colistin, rifampicin and HT0120663 (zidovudine) against log phase NDM-1 *Klebsiella pneumonia* BAA2473 by chequerboard method.

Materials and Methods
1. Bacterial strain used: NDM-1 BAA-2473TM, *Klebsiella pneumoniae* was obtained from the American Type Culture Collection.
2. Growth of bacteria: Log phase growth of BA2473 was carried out according to SOP R-005-00 Log Phase Growth of Bacteria
3. Antibiotics and preparation.

RMP was obtained from Sigma and was dissolved in DMSO to the stock concentration of 10 mg/ml.

Colistin was obtained from Sigma (10 mg/ml).

HT0120663 was obtained from Sigma and was dissolved in DMSO to make stock solution (10 mg/ml).

4. Chequerboard method—as described in Example 1. (Colistin/rifampicin/HT0120663) were tested by a three-dimensional chequerboard method where HT0120663 was added at a single concentration on each plate.

The overnight culture was diluted with nutrient broth (Oxoid) to $10^5$ CFU/ml and 280 µl of the culture suspension was added to each well to make the final volume of 300 µl.

5. Incubation of the compounds with the bacterial suspension was carried out for 24 hours.
6. The effects of combination were examined by calculating the fractional inhibitory concentration index (FICI) of each combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0.

Results

Combination of rifampicin and colistin with no addition of HT0120663. The wells marked yellow in FIG. 12 demonstrate growth. Clear wells indicate growth inhibition or no growth.

Figures 13, 14, 15, 16:
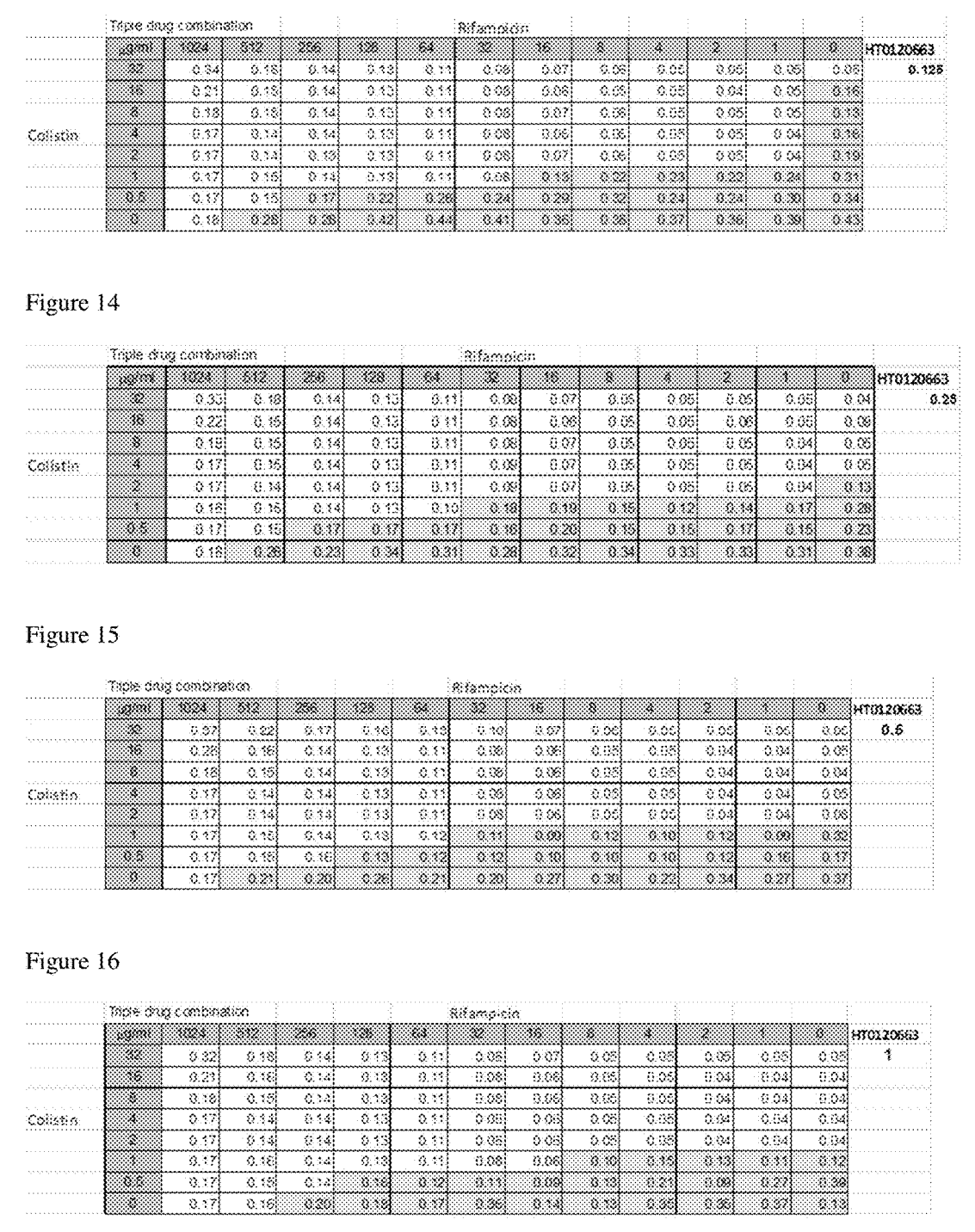

Combination of rifampicin and colistin with addition of HT0120663 at 0.125 µg/ml. The wells marked yellow in FIG. 13 demonstrate growth. Clear wells indicate growth inhibition or no growth.

Addition of HT0120663 at 0.125 µg/ml in rifampicin and colistin combination showed no difference in inhibition of growth.

Combination of rifampicin and colistin with addition of HT0120663 at 0.25 µg/ml. The wells marked yellow in FIG. 14 demonstrate growth. Clear wells indicate growth inhibition or no growth.

Comparing with rifampicin and colistin combination only, addition of HT0120663 at 0.25 µg/ml reduced 4 fold of colistin MIC.

Combination of rifampicin and colistin with addition of HT0120663 at 0.5 µg/ml. The wells marked yellow in FIG. 15 demonstrate growth. Clear wells indicate growth inhibition or no growth.

Comparing with rifampicin and colistin combination, addition of HT0120663 at 0.5 µg/ml reduced 8 fold of colistin MIC.

Combination of rifampicin and colistin with addition of HT0120663 at 1 µg/ml. The wells marked yellow in FIG. 16 demonstrate growth. Clear wells indicate growth inhibition or no growth.

Combination of rifampicin and colistin with addition of HT0120663 at 2 µg/ml. The wells marked yellow in FIG. 17 demonstrate growth. Clear wells indicate growth inhibition or no growth.

Comparing with rifampicin and colistin combination, addition of HT0120663 at 2 µg/ml increased the effect of synergy by reduction of rifampicin MIC.

Combination of rifampicin and colistin with addition of HT0120663 at 4 µg/ml. The wells marked yellow in FIG. 18 demonstrate growth. Clear wells indicate growth inhibition or no growth.

Comparing with rifampicin and colistin combination, addition of HT0120663 at 4 µg/ml increased the effect of synergy by reduction of rifampicin MIC.

Combination of rifampicin and colistin with addition of HT0120663 at 8 µg/ml. Clear wells in FIG. 19 indicate growth inhibition or no growth.

Combination of rifampicin and colistin with addition of HT0120663 at 16 µg/ml. Clear wells in FIG. 20 indicate growth inhibition or no growth.

Figures 21, 22, 23, 24:
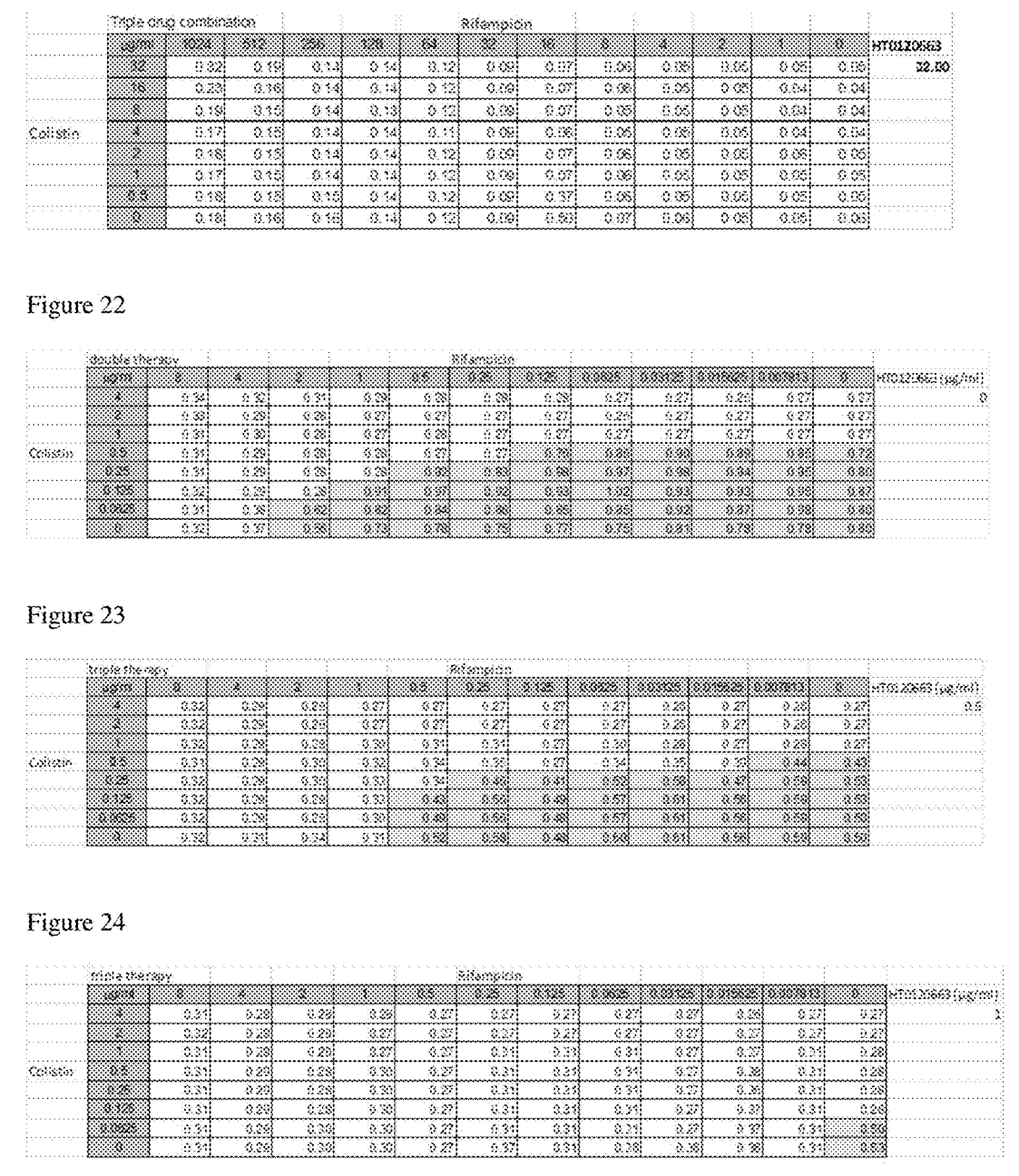

Combination of rifampicin and colistin with addition of HT0120663 at 32 µg/ml. Clear wells in FIG. 21 indicate growth inhibition or no growth.

When HT0120663 was increased to 8 µg/ml, complete inhibition of growth was seen. This was due to the MIC of HT0120663 (8 µg/ml) which on its own inhibited the bacterial growth.

Summary and Conclusion

This data show that three drug combination increased potency of each drug by reduction of MIC. Complete growth inhibition was seen when HT0120663 was added at 8 µg/ml or above.

Example 3; In Vitro Synergy Effect of Colistin, Rifampicin and HT0120663 (Zidovudine) Against Log Phase NDM-1 *Escherichia coli* BAA2471 by Three Dimensional Chequerboard Method Objectives To test the synergy effect of colistin, rifampicin and HT0120663 (zidovudine) against log phase NDM-1 *E. coli* BAA2471 by chequerboard method.

Materials and Methods

1. Bacterial strain used: NDM-1 BAA-2471TM, *E. coli* was obtained from the American Type Culture Collection.
2. Growth of bacteria: Log phase growth of BA2471 was carried out according to SOP R-005-00 Log Phase Growth of Bacteria
3. Antibiotics and preparation.

RMP was obtained from Sigma and was dissolved in DMSO to the stock concentration of 10 mg/ml.

Colistin was obtained from Sigma (10 mg/ml).

HT0120663 was obtained from Sigma and was dissolved in DMSO to make stock solution (10 mg/ml).

4. Chequerboard method—as described in Example 1.

The triple combinations (Colistin/rifampicin/HT0120663) were tested by a three-dimensional chequerboard method where HT0120663 was added at a single concentration on each plate at 0.5, 1, 2, 4, 8, 16 µg/ml, respectively.

The overnight culture was diluted with nutrient broth (Oxoid) to $10^5$ CFU/ml and 280 µl of the culture suspension was added to each well to make the final volume of 300 µl.

5. Incubation of the compounds with the bacterial suspension was carried out for 24 hours.
6. The effects of combination were examined by calculating the fractional inhibitory concentration index (FICI) of double combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0.

Results

Combination of rifampicin and colistin with no addition of HT0120663 against *E. coli* NDM-1 2471. The wells marked yellow in FIG. 22 demonstrate growth. Clear wells indicate growth inhibition or no growth.

MIC of rifampicin was 4 µg/ml. In combination with 0.5 µg/ml of colistin, MIC reduced to 0.25 µg/ml. Colistin MIC was 1 µg/ml. In combination with 2 µg/ml of rifampicin, MIC reduced to 0.125 µg/ml. The FIC index is 0.188

Combination of rifampicin and colistin with addition of HT0120663 at 0.5 µg/ml against *E. coli* NDM-1 2471. The wells marked yellow in FIG. 23 demonstrate growth. Clear wells indicate growth inhibition or no growth.

Addition of HT0120663 at 0.5 µg/ml in rifampicin and colistin combination reduced the MIC of rifampicin from 4 to 1 µg/ml which increased inhibition of growth.

Combination of rifampicin and colistin with addition of HT0120663 at 1 µg/ml against *E. coli* NDM-1 2471. The wells marked yellow in FIG. 24 demonstrate growth. Clear wells indicate growth inhibition or no growth.

Figures 25, 26, 27, 28:
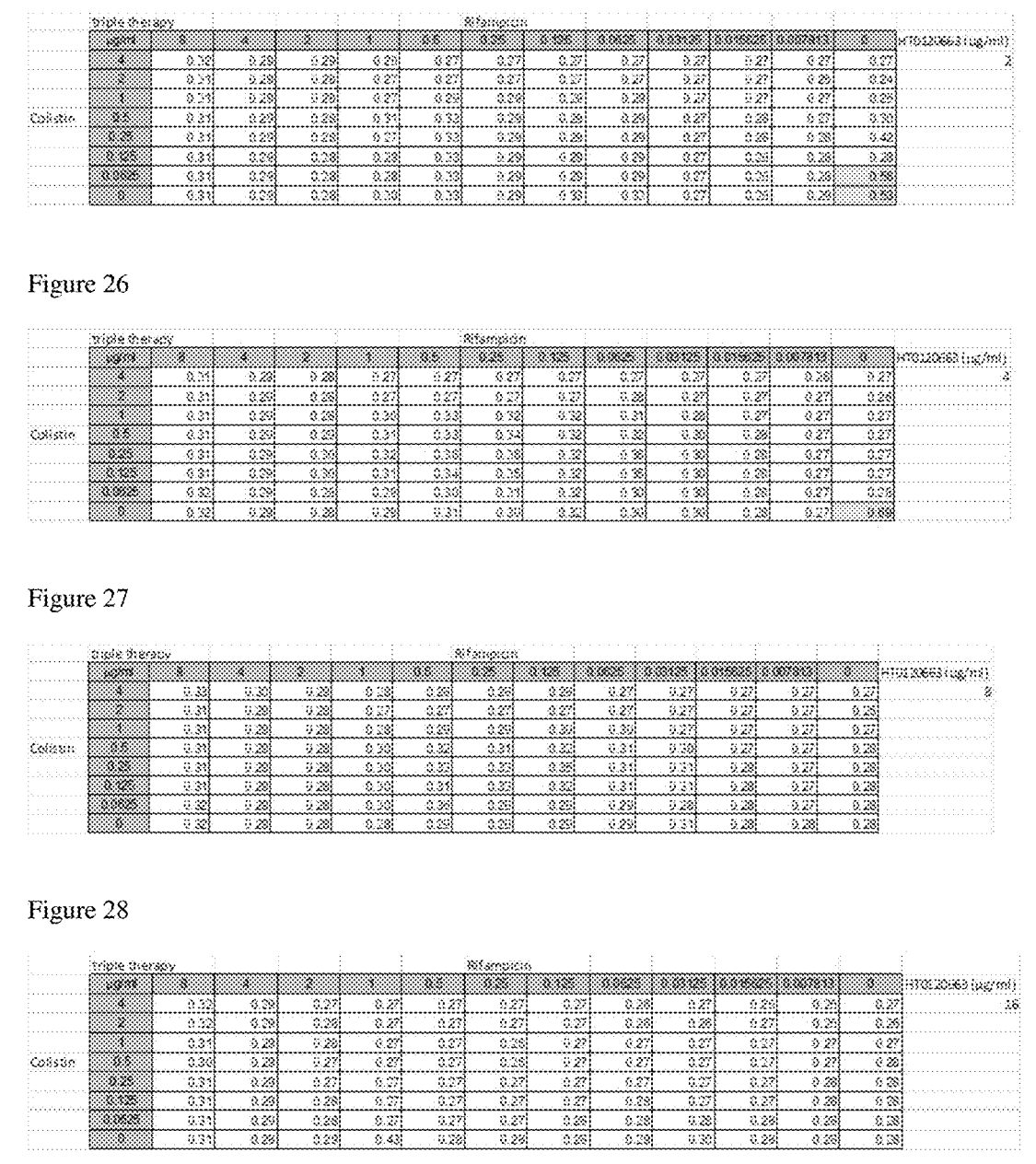

Combination of rifampicin and colistin with addition of HT0120663 at 2 µg/ml against *E. coli* NDM-1 2471. The wells marked yellow in FIG. 25 demonstrate growth. Clear wells indicate growth inhibition or no growth.

Comparing with rifampicin and colistin combination, addition of HT0120663 at 1 and 2 µg/ml inhibited all the growth except the last two wells showing a synergistic triple combination effect.

Combination of rifampicin and colistin with addition of HT0120663 at 4 µg/ml against *E. coli* NDM-1 2471. The wells marked yellow in FIG. 26 demonstrate growth. Clear wells indicate growth inhibition or no growth.

Comparing with rifampicin and colistin combination, addition of HT0120663 at 4 µg/ml inhibited all the growth except the last well where no drugs were present showing a synergistic triple combination effect.

Combination of rifampicin and colistin with addition of HT0120663 at 8 µg/ml. The wells marked yellow in FIG. 27 demonstrate growth. Clear wells indicate growth inhibition or no growth.

Combination of rifampicin and colistin with addition of HT0120663 at 16 µg/ml. The wells marked yellow in FIG. 28 demonstrate growth. Clear wells indicate growth inhibition or no growth.

When HT0120663 was increased to 8 µg/ml or above, complete inhibition of growth was seen. This was due to the MIC of HT0120663 (8 µg/ml) which on its own inhibited the bacterial growth.

Summary and Conclusion

This data show that three drug combination increased potency of each drug by reduction of MIC. Complete growth inhibition was seen when HT0120663 was added at 8 µg/ml or above.

Example 4

Example 4.1: Colistin and Rifampicin Against NDM-1 *Klebsiella pneumonia*

1.1 Chequerboard showing synergy between colistin and rifampicin against NDM-1 *Klebsiella pneumonia* is provided in FIG. 29.

the effect of the combination of colistin and rifampicin against NDM-1 *Klebsiella pneumonia* compared to colistin and rifampicin singly.

Example 4.2: Colistin and Rifampicin Against NDM-1 *Escherichia coli*

2.1 Chequerboard showing synergy between colistin and rifampicin against NDM-1 *E. coli* is provided in FIG. 30.

2.2. FIG. 2 contains time kill curves FIG. 2(*a*), FIG. 2(*b*), FIG. 2(*c*) and FIG. 2(*d*) showing the effect of the combination of colistin and rifampicin against NDM-1 *E. coli* compared to colistin and rifampicin singly.

Example 4.3: Triple Combination (Rifampicin+Colistin+HT0120663 (Zidovudine))

HT0130001=Rifampicin
HT0130002=Colistin
HT0120663=Zidovudine 3. 1 Chequerboard showing synergy between colistin, rifampicin and HT0120663 against NDM-1 *Klebsiella pneumonia* as described in Example 1 is provided in FIGS. 31 to 37.

Example 5

Having demonstrated the effect of adding zidovudine to a combination of colistin and rifampicin, the following examples demonstrate synergy of the latter combination against a variety of drug-resistant bacteria. On the basis of Examples 1-4, the addition of zidovudine would again enhance the double combination of colistin and rifampicin.

Experiment 5.1: In Vitro Synergy Effect of Colistin and Rifampicin Against Log Phase Gram Negative Bacteria by Chequerboard Method Objectives To test the synergy effect of colistin and rifampicin against log phase Gram negative bacteria including *Escherichia coli* and *Klebsiella-Enterobacter-Serratia* group (KES group) by chequerboard method Materials and Methods 1. Bacterial strain used: Clinical antibiotic resistant Gram negative isolates from St George's Hospital. NDM-1 strains were obtained from the American Type Culture Collection BAA-2468TM, *Enterobacter cloacae*. BAA-2469TM *Escherichia coli*. BAA-2470TM, *Klebsiella pneumoniae* subsp. *Pneumonia*. BAA-2471TM, *Escherichia coli*. BAA-2472TM, *Klebsiella pneumoniae* subsp. *Pneumonia*. BAA-2473TM, *Klebsiella pneumoniae* and the National Collection of Type Cultures from NCTC 13443, *Klebsiella pneumonia*
2. Growth of bacteria: Log phase growth of BA2473 was carried out according to SOP R-005-00 Log Phase Growth of Bacteria
3. Antibiotics and preparation.
   i. RMP was obtained from Sigma and was dissolved in DMSO to the stock concentration of 10 mg/ml.
   ii. Colistin was obtained from Sigma (10 mg/ml).

Log phase bacterial culture was incubated with rifampicin and colistin in combinations using chequerboard method.

The overnight culture was diluted with nutrient broth (Oxoid) to $10^5$ CFU/ml and 280 µl of the culture was added to each well to make the final volume of 300 µl.

4. Incubation of the compounds with the bacterial suspension was carried out for 24 hours.
5. The effects of combination were examined by calculating the fractional inhibitory concentration index (FICI) of each combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0.

Results

| Bacterial strains | Number of strains | FIC index <0.5 | >0.5 <2 | >2 | % of strains (synergistic effect) |
|---|---|---|---|---|---|
| *E. coli* | 56 | 55 | 1 | 0 | 98.2 |
| *Klebsiella-Enterobacter-Serratia* (KES group) | 32 | 31 | 1 | 0 | 96.9 |

Summary and Conclusion

1. The synergistic combination of colistin and rifampicin showed in 98.2% of *E. coli* with FIC index less than 0.5.
2. The synergistic combination of colistin and rifampicin showed in 96.9% of the bacteria in KES group with FIC index less than 0.5.

3. Synergistic activities of colistin and rifampicin showed in all NDM-1 strains.

Experiment 5.2: In Vitro Synergy Effect of Colistin and Rifampicin Against Log Phase NDM-1 Strains by Chequerboard Method Objectives To test the synergy effect of colistin and rifampicin against log phase NDM-1 strains by chequerboard method Materials and Methods 1. Bacterial strain used: NDM-1 strains were obtained from the American Type Culture Collection BAA-2468TM, *Enterobacter cloacae*. BAA-2469TM *Escherichia coli*. BAA-2470TM, *Klebsiella pneumoniae* subsp. *Pneumonia*. BAA-2471TM, *Escherichia coll*. BAA-2472TM, *Klebsiella pneumoniae* subsp. *Pneumonia*. BAA-2473TM, *Klebsiella pneumoniae* and the National Collection of Type Cultures from NCTC 13443, *Klebsiella pneumonia*
2. Growth of bacteria: Log phase growth of BA2473 was carried out according to SOP R-005-00 Log Phase Growth of Bacteria
3. Antibiotics and preparation.
   i. RMP was obtained from Sigma and was dissolved in DMSO to the stock concentration of 10 mg/ml.
   ii. Colistin was obtained from Sigma (10 mg/ml).

Log phase bacterial culture was incubated with rifampicin and colistin in combinations using chequerboard method The overnight culture was diluted with nutrient broth (Oxoid) to $10^5$ CFU/ml and 280 µl of the culture was added to each well to make the final volume of 300 µl.

4. Incubation of the compounds with the bacterial suspension was carried out for 24 hours.
5. The effects of combination were examined by calculating the fractional inhibitory concentration index (FICI) of each combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0.

Results

The results are shown in FIGS. 38 to 43.

Summary and Conclusion

Colistin in combination with rifampicin showed FIC index less than 0.5 for BAA2468, BAA2469, BAA2470, BAA2471, BAA2472, BAA2473 and NCTC13443 NDM-1 strains showing a significant synergistic activity.

Example 6: In Vivo Synergy Effect of Colistin, Rifampicin and HT0120663 (Zidovudine) Against NDM-1 *E. coli* in a Mouse Peritoneal Infection Model 180314

Objectives

To investigate the activity of rifampicin, colistin and HT0120663 (zidovudine) in combination against NDM-1 *E. coli* in a mouse peritoneal infection model.

Materials and Methods

1. Mice used: female Imprinting Control Region (ICR) mice aged 6 to 8 weeks were obtained from Harlan UK.
2. Bacterial culture used: NDM-1 BAA2469 *E. coli* was obtained from the American Type Culture Collection.

3. Drug preparation:

HT0120663 (zidovudine) solution was obtained from Pharmacy at the concentration of 10 mg/ml.

Colistin used was Colomycin® (Forest Laboratories UK Ltd) which was dissolved in water to 20 mg/ml.

Rifampicin used was Rifadin® (Sanofi-Aventis) 60 mg/ml.

4. Mouse peritoneal infection model:

Overnight culture of NDM-1 BAA2469 E. coli (200 μl) was injected into the peritoneal cavities of the mice.

5. Drug administration:

At 1.5 hours after infection, the triple combination (colistin/rifampicin/HT0120663) was tested by intravenous administration of rifampicin at 10 mg/kg, colistin at 20 mg/kg and/or HT0120663 at 5 mg/kg singly or in combination to the infected mice. The treatment combinations are shown in Table 1 below.

TABLE 1

|  |  | mg/kg | | |
|---|---|---|---|---|
|  |  | Colistin | Rifampicin | HT0120663 |
| (i) | Colistin | 20 | 0 | 0 |
| (ii) | Rifampicin | 10 | 0 | 0 |
| (iii) | HT0120663 | 0 | 0 | 5 |
| (iv) | Colistin + Rifampicin | 20 | 10 | 0 |
| (v) | Colistin + Rifampicin + HT0120663 | 20 | 10 | 5 |
| (vi) | Control | 0 | 0 | 0 |

6. Organ CFU counting:

At 0 hour, 2 hours and 6 hours after administration of the above treatments (i) to (vi), 1 ml of phosphate buffered saline (PBS) was injected into the peritoneum of the mice followed by gently massaging of the abdomen. Peritoneal fluid was then sampled aseptically. The sampled fluid was diluted and CFU counts were performed in order to determine the effect of the triple combination (colistin/rifampicin/HT0120663).

Figure 3:
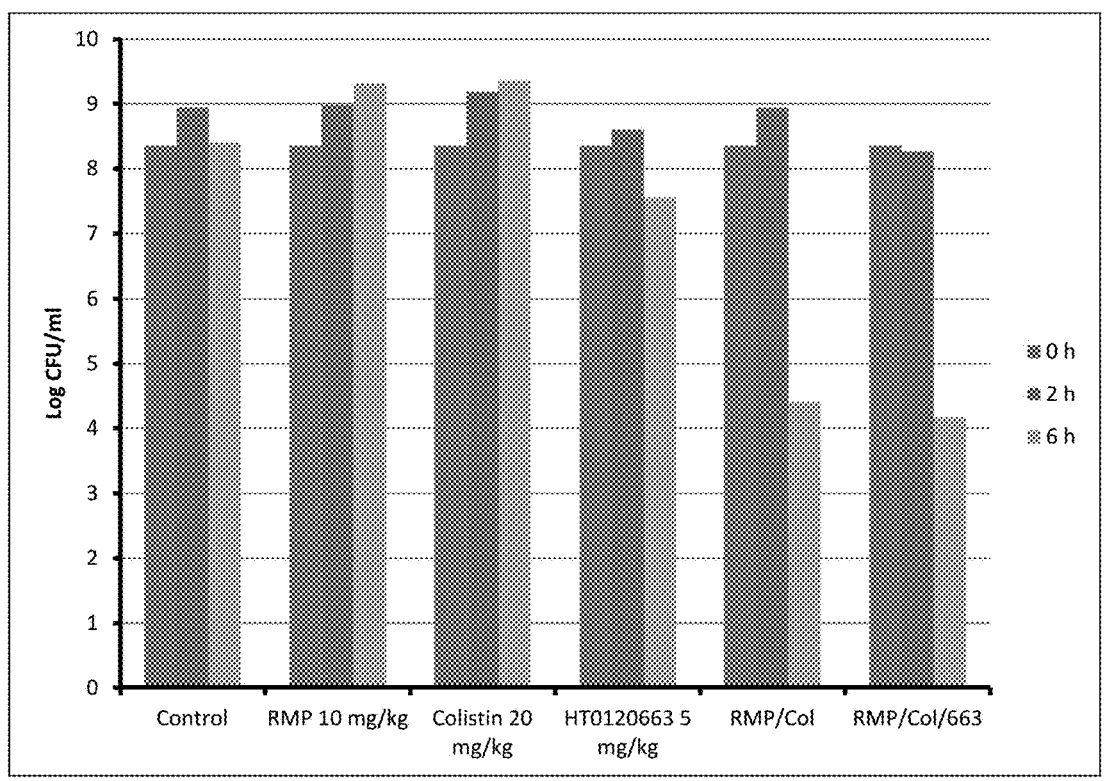
FIG. 3 contains a plot of log CFU/ml for each treatment (i) to (vi). Each treatment was tested, at 0 hour (left bar), 2 hours (middle bar) and 6 hours (right bar) after administration of the respective treatment.

The results are shown in FIG. 3.

Results

FIG. 3 contains a plot of log CFU/ml for each treatment (i) to (vi). Each treatment was tested at 0 hour (left bar), 2 hours (middle bar) and 6 hours (right bar) after administration of the respective treatment.

Summary and Conclusion

1. Administration of rifampicin, colistin or HT0120663 alone showed no in vivo activity against the NDM-1 E. coli.
2. At 2 hours after treatment, there was no significant difference between rifampicin, colistin or HT0120663 alone and the combinations.
3. At 6 hours after treatment, the rifampicin and colistin combination (RMP/Col) killed 4.5 log more bacteria than the single drugs.
4. At 6 hours after treatment, the triple combination of rifampicin/colistin/HT0120663 (RMP/Col/663) killed 4.5 log more bacteria than rifampicin or colistin singly and 3 logs more than HT0120663. The triple combination also killed more bacteria than the double combination of RMP/Col.

Example 7: In Vivo Synergy Effect of Colistin, Rifampicin and HT0120663 (Zidovudine) Against NDM-1 Klebsiella pneumonia in a Mouse Peritoneal Infection Model 180314

Objectives

To investigate the activity of rifampicin, colistin and HT0120663 (zidovudine) in combination against NDM-1 Klebsiella pneumonia in a mouse peritoneal infection model.

Materials and Methods

1. Mice used: female ICR mice aged 6 to 8 weeks were obtained from Harlan UK.
2. Bacterial cultures used: NDM-1 BAA2470 K. pneumoniae obtained from the American Culture Collection.
3. Drug preparation:

HT0120663 solution was obtained from Pharmacy at the concentration of 10 mg/ml. Colistin used was Colomycin® (Forest Laboratories UK Ltd) which was dissolved in water to 20 mg/ml.

Rifampicin used was Rifadin® (Sanofi-Aventis) 60 mg/ml.

4. Mouse peritoneal infection model:

Overnight culture of NDM-1 BAA2470 K. pneumoniae (200 μl) was injected into the peritoneal cavities of the mice.

5. Drug administration

At 1.5 hours after infection, the triple combination (colistin/rifampicin/HT0120663) was tested by intravenous administration of rifampicin at 10 mg/kg, colistin at 20 mg/kg and/or HT0120663 at 5 mg/kg singly or in combination to the infected mice as shown in Table 2.

TABLE 2

|  |  | mg/kg | | |
|---|---|---|---|---|
|  |  | Colistin | Rifampicin | HT0120663 |
| (i) | Colistin | 20 | 0 | 0 |
| (ii) | Rifampicin | 10 | 0 | 0 |
| (iii) | HT0120663 | 0 | 0 | 5 |
| (iv) | Colistin + Rifampicin | 20 | 10 | 0 |
| (v) | Colistin + Rifampicin + HT0120663 | 20 | 10 | 5 |
| (vi) | Control | 0 | 0 | 0 |

6. Organ CFU counting:

At 0 hour, 2 and 6 hours after administration of the above treatments (i) to (vi), 1 ml of phosphate buffered saline (PBS) was injected into the peritoneum of the mice followed by gently massaging of the abdomen. Peritoneal fluid was then sampled aseptically. The sampled fluid was diluted and CFU counts were performed in order to determine the effect of the triple combination (colistin/rifampicin/HT0120663).

Figure 4:
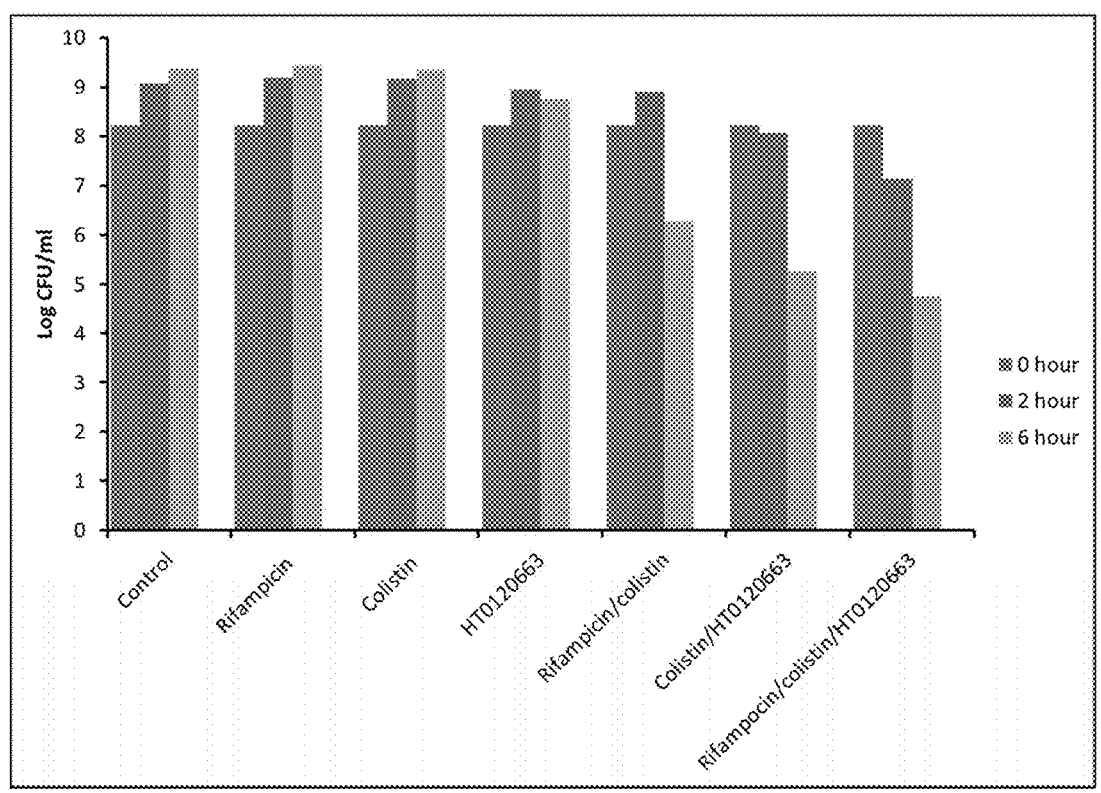
FIG. 4 contains a plot of log CFU/ml for each treatment (i) to (vi) at 0 hour, (left bar), 2 hours (middle bar) and 6 hours (right bar) after administration of the respective treatment.

The results are shown in FIG. 4.

Results

FIG. 4 contains a plot of log CFU/ml for each treatment (i) to (vi) at 0 hour, (left bar), 2 hours (middle bar) and 6 hours (right bar) after administration of the respective treatment.

Summary and Conclusions

1. Administration of rifampicin, colistin or HT0120663 alone showed no in vivo activity against the NDM-1 K. pneumoniae.
2. At 2 hours after treatment, there was no significant difference between the colistin and rifampicin combination or colistin and HT0120663, singly or in combination. However, the triple combination (rifampicin/colistin/HT0120663) reduced 1 log of initial inoculum.
3. At 6 hours after treatment, the rifampicin and colistin combination killed 3.1 log more bacteria than the single drugs.
4. At 6 hours after treatment, the colistin and HT0120663 combination killed 4.1 log more bacteria than each single drug.
5. At 6 hours after treatment, the triple combination of rifampicin/colistin/HT0120663 killed 4.6 log more bacteria than rifampicin, colistin or HT0120663 singly and also more bacteria than the double combinations of rifampicin/colistin and colistin/HT0120663.

Faced with the challenge of improving anti-microbial therapy in view of the increase in multidrug resistant strains, the Examples demonstrate a significant effect of adding zidovudine to a therapeutic regimen consisting of colistin and an anti-tuberculosis antibiotic such as rifampicin or rifapentine or rifabutin. For the first time, the addition of zidovudine has been shown to have a synergisitc effect on this regimen. This triple combination may therefore offer a significant improvement to the treatment of anti-microbial infections arising from a range of bacteria in addition to those utilised in the Examples.

The invention claimed is:
1. A method of treating a bacterial infection, which comprises administering to a mammal having said bacterial infection a combination of:
zidovudine;
a polymyxin selected from colistin or polymyxin B, or a pharmaceutically acceptable salt thereof;
an anti-tuberculosis antibiotic selected from rifampicin, rifapentine and rifabutin; and optionally piperine, wherein the bacterial infection is caused by Enterobacteriaceae.
2. A product comprising zidovudine in combination with:
a polymyxin selected from colistin and polymyxin B or a pharmaceutically acceptable salt thereof;
an anti-tuberculosis antibiotic selected from rifampicin, rifapentine and rifabutin; and optionally piperine;
as a combined preparation for simultaneous, separate or sequential use in killing clinically latent bacteria associated with a bacterial infection, wherein the clinically latent bacteria are Enterobacteriaceae.
3. A pharmaceutical composition comprising zidovudine in combination with:
a polymyxin selected from colistin and polymyxin B or a pharmaceutically acceptable salt thereof;
an anti-tuberculosis antibiotic selected from rifampicin, rifapentine and rifabutin; and optionally piperine; and
a pharmaceutically acceptable carrier for use in treating a bacterial infection, wherein the bacterial infection is caused by Enterobacteriaceae.
4. The method according to claim 1, wherein treating the bacterial infection comprises killing clinically latent bacteria associated with the bacterial infection, wherein the clinically latent bacteria are Enterobacteriaceae.
5. The method according to claim 1, wherein zidovudine is administered in combination with colistin and either rifampicin or rifapentine.
6. A composition comprising zidovudine, colistin, and either rifampicin or rifapentine for simultaneous, separate or sequential use in treating a bacterial infection, wherein the bacterial infection is caused by Enterobacteriaceae.
7. A method of treating a bacterial infection, which comprises administering to a mammal having said bacterial infection a combination of: zidovudine; colistin; and either rifampicin or rifapentine, wherein the bacterial infection is caused by Enterobacteriaceae.
8. The method according to claim 1 or 7, further comprising administering piperine to said mammal.
9. The method according to claim 1 or claim 7, wherein the bacterial infection is caused by *E. coli, Proteus* or *Klebsiella*.
10. The method according to claim 1 or claim 7, wherein the infection is caused by *E. coli* or *Klebsiella*.
11. The method according to claim 1 or claim 7, wherein the infection is caused by a drug-resistant strain.
12. The method according to claim 11, wherein the infection is caused by a carbapenemase-resistant strain or "extended spectrum β-lactamase" (ESPL) strain.
13. The method according to claim 1 or claim 7, for the treatment of a urinary tract infection, nephritis, a kidney stone associated infection or a catheter-associated infection caused by Enterobacteriaceae.
14. The product according to claim 2, further comprising piperine.
15. The pharmaceutical composition according to claim 3, further comprising piperine.
16. The method according to claim 12, wherein the strain is New Delhi Metallo-beta-lactamase-1 (NDM-1) resistant *Klebs. Pneumonia*.

* * * * *